United States Patent
Luo

(10) Patent No.: US 10,202,652 B2
(45) Date of Patent: Feb. 12, 2019

(54) METHODS AND COMPOSITIONS OF PREDICTING ACTIVITY OF RETINOID X RECEPTOR MODULATOR

(75) Inventor: Wen Luo, San Diego, CA (US)

(73) Assignee: Denovo Biopharma (Hangzhou) Ltd. Co. (CN)

( * ) Notice: Subject to any disclaimer, the term of this patent is extended or adjusted under 35 U.S.C. 154(b) by 518 days.

(21) Appl. No.: 14/124,668

(22) PCT Filed: Jun. 7, 2012

(86) PCT No.: PCT/US2012/041379
§ 371 (c)(1),
(2), (4) Date: Mar. 14, 2014

(87) PCT Pub. No.: WO2012/170704
PCT Pub. Date: Dec. 13, 2012

(65) Prior Publication Data
US 2015/0368720 A1    Dec. 24, 2015

Related U.S. Application Data

(60) Provisional application No. 61/494,773, filed on Jun. 8, 2011.

(51) Int. Cl.
| | | |
|---|---|---|
| C12Q 1/68 | (2018.01) | |
| C40B 30/04 | (2006.01) | |
| C12Q 1/6886 | (2018.01) | |
| C07K 14/705 | (2006.01) | |
| G06F 19/00 | (2018.01) | |
| G16H 50/20 | (2018.01) | |

(52) U.S. Cl.
CPC ...... *C12Q 1/6886* (2013.01); *C07K 14/70567* (2013.01); *G06F 19/704* (2013.01); *G16H 50/20* (2018.01); *C12Q 2600/106* (2013.01); *C12Q 2600/136* (2013.01); *C12Q 2600/156* (2013.01); *C12Q 2600/178* (2013.01); *C40B 30/04* (2013.01); *G01N 2500/00* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,790,396 B1 | 9/2010 | Ramsey et al. |
| 2008/0280955 A1 | 11/2008 | McCamish |
| 2008/0299125 A1 | 12/2008 | Hinds et al. |

FOREIGN PATENT DOCUMENTS

| | | | |
|---|---|---|---|
| WO | WO-2009/134774 | 11/2009 | |
| WO | WO-2011/006157 | 1/2011 | |
| WO | WO-2011/056688 | 5/2011 | |
| WO | WO 2011056688 A2 * | 5/2011 | ....... G01N 33/57484 |

OTHER PUBLICATIONS

McClay et al., "Genome-wide pharmacogenomic analysis of response to treatment with antipsychotics," Molecular Psychiatry 2011, 16:76-85, published online Sep. 1, 2009.*
Han et al., "Associations of ABCB1, ABCB2, and ABCG2 Polymorphisms With Irinotecan-Pharmacokinetics and Clinical Outcome in Patients With Advanced Non-Small Cell Lung Cancer," Cancer (2007) 110(1):138-147.
Kojima et al., "Determination of genomic breakpoints in an epileptic patient using genotyping array," Biochemical and Biophysical Research Communications (2006) 341:792-796.
McClay et al., "Genome-wide pharmacogenomic analysis of response to treatment with antipsychotics," Molecular Psychiatry (2011) 16:76-85.
Patent Examination Report No. 1 for AU 2012267877, issued Dec. 3, 2014, 6 pages.
Supplementary European Search Report for EP 12797326.1, dated Dec. 3, 2014, 8 pages.
Wei et al., "Predictive value of ERCC1 and XPD polymorphism in patients with advanced non-small cell lung cancer receiving platinum-based chemotherapy: a systemic review and meta-analysis," Med. Oncol. (2011) 28:315-321.
Communication pursuant to Article 94(3) EPC for EP 12 702 740.7, dated Feb. 5, 2015, 9 pages.
Restriction Requirement for U.S. Appl. No. 13/982,470, dated Jun. 24, 2015, 8 pages.
Search Report and Written Opinion for SG 2013057658, dated Feb. 17, 2015, 13 pages.
Sorensen et al., "Whole Genome Amplification on DNA from Filter Paper Blood Spot Samples: An Evaluation of Selected Systems," Genetic Testing (2007) 11(1):65-71.
Communication pursuant to Article 94(3) EPC for EP 12797326.1, dated Dec. 18, 2015, 6 pages.
Notice of Acceptance for AU 2012267877, dated Dec. 9, 2015, 2 pages.
Patent Examination Report No. 2 for AU 2012267877, dated Nov. 20, 2015, 4 pages.
Teslovich et al., "Biological, Clinical, and Population Relevance of 95 Loci for Blood Lipids," Nature (2010) 466(7307):707-713.
Examination Report for CN 201280027212.8, dated Mar. 3, 2015, 4 pages.
Al-Safar et al., "Evaluation of different sources of DNA for use in genome wide studies and forensic application," Appl Microbiol Biotechnol (2011) 89(3):807-815.
Altucci et al., "RAR and RXR modulation in cancer and metabolic disease," Nat Rev Drug Discov (2007) 6:793-810.

(Continued)

*Primary Examiner* — Kaijiang Zhang
(74) *Attorney, Agent, or Firm* — Rimon, P.C.

(57) ABSTRACT

The present invention describes genomic biomarkers that have been discovered to correlate with varied individual responses (efficacy, adverse effect, and other end points) to therapeutic retinoid X receptor modulator, such as bexarotene, in treating diseases such as, non small cell lung cancer. The newly discovered biomarkers and others in linkage disequilibrium with them can be used in companion diagnostic tests which can help to predict drug responses and apply drugs only to those who will be benefited, or exclude those who might have adverse effects, by the treatment.

18 Claims, 5 Drawing Sheets

Specification includes a Sequence Listing.

(56) References Cited

OTHER PUBLICATIONS

Ardlie et al., "Patterns of linkage disequilibrium in the human genome," Nat Rev Genet (2002) 3(4):299-309.
Bergen et al., "Comparison of yield and genotyping performance of multiple displacement amplification and OmniPlex whole genome amplified DNA generated from multiple DNA sources," Hum Mutat (2005) 26(3):262-270.
Blumenschein et al., "Phase III trial comparing carboplatin, paclitaxel, and bexarotene with carboplatin and paclitaxel in chemotherapy-naive patients with advanced or metastatic non-small-cell lung cancer: SPIRIT II," J Clin Oncol (2008) 26:1879-1885.
Boehm et al., "Synthesis and structure-activity relationships of novel retinoid X receptor-selective retinoids," J Med Chem (1994) 37(18):2930-2941.
Bucasas et al., "Assessing the utility of whole-genome amplified serum DNA for array-based high throughput genotyping," BMC Genetics (2009) 10(1):85.
Carulli et al., "Chenodeoxycholic acid and ursodeoxycholic acid effects in endogenous hypertriglyceridemias. A controlled double-blind trial," J Clin Pharmacol (1981) 21:436-442.
Chiang "Bile acid regulation of gene expression: roles of nuclear hormone receptors," Endocr Rev (2002) 23(4):443-463.
Cramer et al., "ApoE-directed therapeutics rapidly clear β-amyloid and reverse deficits in AD mouse models," Science (2012) 335(6075):1503-1506.
Croft et al., "Performance of whole-genome amplified DNA isolated from serum and plasma on high-density single nucleotide polymorphism arrays," J Mol Diagn (2008) 10(3):249-257.
Delanote et al., "Plastins: versatile modulators of actin organization in (patho) physiological cellular processes," Acta Pharmacal Sin (2005) 26:769-779.
Duane et al., "Diminished gene expression of ileal apical sodium bile acid transporter explains impaired absorption of bile acid in patients with hypertriglyceridemia," J Lipid Res (2000) 41:1384-1389.
Duvic et al., "Bexarotene is effective and safe for treatment of refractory advanced-stage cutaneous T-cell lymphoma: multinational phase II-III trial results," J Clin Oncol (2001) 19(9):2456-2471.
Edelman et al., "Phase II trial of the novel retinoid, bexarotene, and gemcitabine plus carboplatin in advanced non-small cell lung cancer," J Clin Oncol (2005) 23:5774-5778.
Gan et al., "Class III beta-tubulin mediates sensitivity to chemotherapeutic drugs in non small cell lung cancer," Cancer Res (2007) 67:9356-9363.
Govindan et al., "Phase II Trial of Bexarotene Capsules in Patients With Advanced Non-Small-Cell Lung Cancer After Failure of Two or More Previous Therapies," J Clin Oncol (2006) 24:4848-4854.
Guessous et al., "Genome-wide association studies in pharmacogenomics: untapped potential for translation," Genome Med (2009) 1(4):46-46.4.
Hollegaard et al., "Genome-wide scans using archived neonatal dried blood spot samples," BMC Genomics (2009) 10(1):297-302.
Hollegaard et al., "High-throughput genotyping on archived dried blood spot samples," Genet Test Mol Biomarkers (2009) 13(2):173-179.
International Preliminary Report on Patentability for PCT/US2012/023195, dated Aug. 6, 2013, 8 pages.
International Search Report and Written Opinion for PCT/US2012/023195, dated May 21, 2012, 13 pages.
International Search Report and Written Opinion for PCT/US2012/041379, dated Nov. 9, 2012, 7 pages.
International Preliminary Report on Patentability for PCT/US2012/041379, dated Dec. 10, 2013, 5 pages.
Jung et al., "Human apical sodium-dependent bile salt transporter gene (SLC10A2) is regulated by the peroxisome proliferator-activated receptor alpha," J Biol Chem (2002) 277:30559-30566.
Kast et al., "Farnesoid X-activated receptor induces apolipoprotein C-II transcription: a molecular mechanism linking plasma triglyceride levels to bile acids," Mol Endocrinol (2001) 15(10):1720-1728.
Khuri et al., "Multi-institutional phase 1/II trial of oral bexarotene in combination with cisplatin and vinorelbine in previously untreated patients with advanced non-small cell lung cancer," J Clin Oncol (2001) 19(10):2626-2637.
Korn et al., "Integrated genotype calling and association analysis of SNPs, common copy number polymorphisms and rare CNVs," Nat Genet (2008) 40(10):1253-1260.
Lasken et al., "Whole genome amplification: abundant supplies of DNA from precious samples or clinical specimens," Trends Biotechnol (2003) 21(12):531-535.
Love et al., "Analysis of the ileal bile acid transporter gene, SLC10A2, in subjects with familial hypertriglyceridemia," Arterioscler Thromb Vasc Biol (2001) 21(12):2039-2045.
Lu et al., "Use of whole genome amplification to rescue DNA from plasma samples," Biotechniques (2005) 39(4):511-515.
Luo et al., "Identification of polymorphisms associated with hypertriglyceridemia and prolonged survival induced by bexarotene in treating non-small cell lung cancer," Anticancer Res (2011) 31(6):2303-2311.
McLeod et al., "Selection of markers to predict tumour response or survival: description of a novel approach," Eur J Cancer (1999) 35(12):1650-1652.
Mead et al., "Genetic risk factors for variant Creutzfeldt-Jakob disease: a genome-wide association study," Lancet Neurology (2009) 8(1):57-66.
Miller et al., "Initial clinical trial of a selective retinoid X receptor ligand, LGD1069," J Clin Oncol (1997) 15(2):790-795.
Neimark et al., "Bile acid-induced negative feedback regulation of the human ileal bile acid transporter," Hepatology (2004) 40:149-156.
Park et al., "Comparing whole-genome amplification methods and sources of biological samples for single-nucleotide genotyping," Clin Chem (2005) 51:1520-1523.
Pinaire et al., "Therapeutic potential of retinoid x receptor modulators for the treatment of the metabolic syndrome," PPAR Res (2007) 2007:94156, 12 pages.
Prislei et al., "From plasma membrane to cytoskeleton: a novel function for semapholin 6A," Mol Cancer Ther (2008) 7:233-241.
Purcell et al., "PLINK: a tool set for whole-genome association and population-based linkage analyses," Am J Hum Genet (2007) 81(3):559-575.
Rabbee et al., "A genotype calling algorithm for Affymetrix SNP arrays," Bioinformatics (2006) 22(1):7-12.
Ramlau et al., "Randomized phase III trial comparing bexarotene (L1069-49)/cisplatin/vinorelbine with cisplatin/vinorelbine in chemotherapy-naive patients with advanced or metastatic non-small-cell lung cancer: SPIRIT I," J Clin Oncol (2008) 26:1886-1892.
Rizvi et al. "A Phase I study of LGD 1069 in adults with advanced cancer," Clin Cancer Res (1999) 5:1658-1664.
Samstag et al., "Ectopic expression of L-plastin in human tumor cells: diagnostic and therapeutic implications," Advan Enzyme Regul (2007) 47:118-126.
Simon et al., "Use of archived specimens in evaluation of prognostic and predictive biomarkers," JNCI (2009) 101(21):1446-1452.
Singer et al., "A genome-wide study identifies HLA alleles associated with lumiracoxib-related liver injury," Nat Genet (2010) 42(8):711-714.
Sjoholm et al., "Comparison of archival plasma and formalin-fixed paraffin-embedded tissue for genotyping in hepatocellular carcinoma," Cancer Epidemiol Biomarkers Prev (2005) 14(1):251-255.
Skol et al., "Joint analysis is more efficient than replication-based analysis for two-stage genome-wide assoication studies," Nature Genetics (2006) 38(2):209-213.
Verrills et al., "Alterations in gamma-actin and tubulin-targeted drug resistance in childhood leukemia," J Natl Cancer Inst (2006) 98:1363-1374.
Watanabe et al., "Bile acids lower triglyceride levels via a pathway involving FXR, SHP, and SREBP-1c," J Clin Invest (2004) 113:1408-1418.

(56) References Cited

OTHER PUBLICATIONS

Wu et al., "Suppression of mammary tumorigenesis in transgenic mice by the RXR-selective retinoid, LGD1069," Cancer Epidemiol Biomarkers Prev (2002) 11:467-474.
Yen et al., "The selective retinoid X receptor agonist bexarotene (LGD1069, Targretin) prevents and overcomes multidrug resistance in advanced breast carcinoma," Mol Cancer Ther (2005) 4(5):824-834.
Rigas and Dragnev, "Emerging Role of Rexinoids in Non-Small Cell Lung Cancer," The Oncologist (2005) 10:22-33.
Turner et al., "Quality Control Procedures for Genome-Wide Association Studies," Current Protocols in Human Genetics (2011) Suppl. 68:1.191-1.19.18.
Response to Communication pursuant to Article 94(3) EPC, filed Aug. 14, 2015, 41 pages.
Response to Restriction Requirement for US 13/982,470, filed Aug. 24, 2015, 8 pages.
Response to Office Action for AU 2012267877, filed Nov. 25, 2015, 12 pages.
Communication pursuant to Article 94(3) EPC, dated Jan. 25, 2016, 10 pages.
Notice of Reasons for Rejection (translation) for JP 2013-551420, dated Feb. 3, 2016, 11 pages.
Office Action for U.S. Appl. No. 13/982,470, dated Feb. 24, 2016, 12 pages.
Notice of Reasons for Rejection (translation) for JP 2014-514846, dated Mar. 30, 2016, 12 pages.
Notice of Grant for AU 2012267877, dated Apr. 7, 2016, 1 page.
Notification of Defects (translation) in IL 227696, dated May 1, 2016, 3 pages.
Response to Office Action for U.S. Appl. No. 13/982,470, filed May 24, 2016, 24 pages.
Response to Communication pursuant to Article 94(3) EPC, filed Jul. 27, 2016, 17 pages.
Final Office Action for U.S. Appl. No. 13/982,470, dated Sep. 9, 2016, 11 pages.
Response to Notice of Reasons for Rejection for JP 2013-551420, filed Aug. 2, 2016, 14 pages.
Response to Office Action for JP 2014-514846, filed Sep. 29, 2016, 48 pages.
Affymetrix, "GeneChip Human Mapping 500K Array Set," dated Nov. 21, 2016. Retrieved on http://www.affymetrix.com/estore/browse/productPrinter.jsp?productId=131459&clickTabsId=p7tpb1_1.
Yang et al., "Genome-wide interrogation of germline genetic variation associated with treatment response in childhood acute lymphoblastic leukemia," JAMA (2009) 301(4):393-403.
Summons to attend oral proceedings pursuant to Rule 115(1) EPC for EP 12797326.1, dated Feb. 9, 2017, 7 pages.
Notice of Reasons for Rejection for JP 2014-514846, dated Feb. 28, 2017, 17 pages (Including English translation).
Request for Continued Examination for U.S. Appl. No. 13/982,470, dated Mar. 8, 2017, 18 pages.
Summons to attend oral proceedings pursuant to Rule 115(1) EPC for EP 12702740.7, dated Jan. 25, 2017, 9 pages.
Response to Summons to attend oral proceedings pursuant to Rule 115(1) EPC for EP 12702740.7, dated Jun. 6, 2017, 16 pages.
Communication under Rule 71(3) EPC for EP 12702740.7, dated Jul. 31, 2017, 6 pages.
Response to Notification of Defects in IL 227696, dated Nov. 30, 2016, 4 pages.
Notification of Defects in IL 227696, dated Jan. 25, 2017, 4 pages (English translation).
Office Action for MX 75734, dated Sep. 23, 2016, 4 pages.
Invitation to Respond to Written Opinion for SG 2013057658, dated Mar. 10, 2017, 16 pages.
Response to Invitation to Respond to Written Opinion for SG 2013057658, dated Aug. 10, 2017, 14 pages.
Office Action for JP 2016-151735, dated May 1, 2017, 3 pages (Including English translation).
Ef-Hefnawy, et al., "Characterization of Amplifiable, Circulating RNA in Plasma and Its Potential as a Tool for Cancer Diagnostics," Clinical Chemistry, 2004, vol. 50, No. 3, pp. 564-573.
Canadian Patent Office, Response to Office Action for CA Application No. 2,826,109, dated May 4, 2018, 18 pages.
Korean Intellectual Property Office, Response to Office Action for KR Application No. 10-2013-7023254, dated May 29, 2018, 28 pages (partial English translation attached).
Japan Patent Office, Response to Office Action for JP Application No. 2016-151735, dated Jun. 27, 2018, 4 pages.
Japan Patent Office, Claim Amendments for Response to Office Action for JP Application No. 2016-151735, dated Jun. 27, 2018, 2 pages.
European Patent Office, Communication under Rule 71(3) EPC, Notice of Intent to Grant a European Patent for EP Application No. 12702740.7, dated Jul. 31, 2017, 6 pages.
European Patent Office, Text of patent intended for grant accompanying EPO Communication under Rule 71 (3) EPC for EP Application No. 12702740.7, dated Jul. 31, 2017, 83 pages.
Canadian Patent Office, Office Action for CA Application No. 2,826,109, dated Nov. 8, 2017, 4 pages.
Korean Intellectual Property Office, Office Action for KR Application No. 10-2013-7023254, dated Jan. 29, 2018, 30 pages (English translation attached).

* cited by examiner

METHODS AND COMPOSITIONS OF PREDICTING ACTIVITY OF RETINOID X RECEPTOR MODULATOR

CROSS-REFERENCE TO RELATED APPLICATIONS

This application is the national phase of PCT application PCT/US2012/041379 having an international filing date of Jun. 7, 2012, which claims priority to U.S. Provisional Application No. 61/494,773, filed on Jun. 8, 2011. The entire contents of the above-listed applications are incorporated herein by this reference in their entireties.

RELATED PATENT APPLICATIONS

This patent application claims the benefit of U.S. Provisional Patent Application No. 61/494,773, filed Jun. 8, 2011, which is hereby incorporated by reference in its entirety, including all drawings and cited publications and documents.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 669602000200SeqList.txt, date recorded: Dec. 6, 2013, size: 4,455 bytes).

TECHNICAL FIELD

The present invention relates to the field of pharmacogenomics, which applies one or more genomic biomarkers and the related diagnostic methods, devices, reagents, systems, and kits, for predicting varied individual responses such as, for example, efficacy or adverse effect, to therapeutic agents.

BACKGROUND ART

The retinoid X receptor (RXR), a member of the nuclear-receptor superfamily, is a common binding partner for a subgroup of other nuclear receptors. RXR is able to form heterodimers with a number of nuclear receptors, such as retinoid acid receptors, peroxisome proliferator-activated receptors (PPAR), Liver X receptors (LXR), and farnesoid X receptor (FXR), and is a pleiotropic regulator involved in many biological pathways. With the development of RXR-specific agonists, such as bexarotene, tremendous potential exists to benefit many critical therapeutic areas, including metabolic syndrome, dermatologic disease, neurodegenerative diseases and disorders, treatment of tumors, and cancer prevention (13, 14, 30).

Bexarotene (also called Targretin, LGD1069) is a selective modulator of retinoid X receptors (RXRs) approved for treating refractory advanced-stage cutaneous T-cell lymphoma (1, 2). A number of preclinical studies and phase I and II clinical trials have shown that bexarotene also exhibits promising antitumor or tumor prevention activity for breast cancer, renal cell carcinoma and lung cancer (3-8). Consequently, two large phase III trials (SPIRIT I and SPIRIT II) were conducted to evaluate the efficacy and safety of standard chemotherapy agents with or without bexarotene as a first-line therapy in treating advanced non small cell lung cancer. The results from both phase III trials, however, showed that the addition of bexarotene to chemotherapy did not improve overall survival in the intent-to-treat population, the primary efficacy endpoint (9, 10). A known side-effect of retinoid therapy is the elevation of serum lipids, and the majority of the bexarotene treated patients in the two SPIRIT trials developed hypertriglyceridemia, as expected. Further analysis revealed that 30-40% of the patients appeared to be more sensitive to bexarotene treatment and developed NCI grade 3 or higher hypertriglyceridemia. Survival analysis in this subgroup of patients in each of the two trials revealed significantly longer survival compared to the patients in the control arm and to patients with low-grade hypertriglyceridemia (9, 10). This intriguing correlation between survival and triglyceride level induced by bexarotene observed in both SPIRIT trials is illustrated in FIG. 1A. Similar correlations were also revealed by retrospective analysis in other bexarotene cancer trials (11). These findings prompted the search for biomarkers which can predict bexarotene sensitivity and identify a subgroup of non small cell lung cancer patients whose survival could be prolonged by bexarotene treatment.

SUMMARY OF THE INVENTION

In one aspect, the present invention provides a panel of isolated biomarkers comprising two, three, four or more single nucleotide polymorphisms (SNPs) selected from the group consisting of rs7434820, rs4572960, rs10058324, rs1051853, rs6997581, rs2631686, rs1795505, rs1184776, rs7334509, rs6491738, rs7333033, rs7338381, rs3916931 and rs1506011, or complimentary sequences thereof, and/or in linkage disequilibrium therewith. In some embodiments, the panel may comprise all the SNPs, or complimentary sequences thereof, and/or in linkage disequilibrium therewith. In some embodiments, the SNPs may comprise the nucleotide sequences set forth in SEQ ID NOs:1-14, respectively, or complimentary sequences thereof, and/or in linkage disequilibrium therewith. Further provided herein is a panel of biomarkers, e.g., SNPs, associated and/or linked with two, three, four or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931 and rs1506011, or in linkage disequilibrium therewith.

In another aspect, provided herein is a microarray for the assessment of the panel of isolated biomarkers disclosed herein, which comprises a combination of molecules on a substrate, wherein said molecules are used for assaying the SNPs. In some embodiments, the molecules may be oligonucleotides or polypeptides. In some embodiments, the oligonucleotides may comprise the nucleotide sequences set forth in SEQ ID NOs:1-14, or complimentary sequences thereof.

In a further aspect, provided herein is a reagent for the assessment of the panel of isolated biomarkers disclosed herein, which may comprise one or more molecules for assaying the SNPs. In some embodiments, the molecules may be oligonucleotides or polypeptides. In some embodiments, the oligonucleotides may comprise the nucleotide sequences set forth in SEQ ID NOs:1-14, or complimentary sequences thereof. In some embodiments, the SNPs may be assayed by sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

In an additional aspect, provided herein is a kit for the assessment of a panel of isolated biomarkers, which comprises the reagent disclosed herein, wherein the biomarkers may comprise one or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, rs1506011, or in linkage disequilibrium therewith. In some embodiments, the kit may further comprise instructions for using the biomarker to conduct a companion diagnostic test.

In yet another aspect, provided herein is a companion diagnostic test for a treatment using a panel of isolated biomarkers comprising one, two, three, four or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931 and rs1506011, or in linkage disequilibrium therewith. In some embodiments, the panel may comprise all the SNPs, or complimentary sequences thereof. Further provided herein is a companion diagnostic test for a treatment using one or more isolated biomarkers associated and/or linked with one, two, three, four or more of the SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, rs1506011, or in linkage disequilibrium therewith. In some embodiments, the companion diagnostic test may comprise: a) obtaining a biological sample from a subject that is undergoing a treatment or is considered for a treatment; b) isolating genomic DNA from said biological sample; c) assaying the panel of biomarkers; d) generating an output with a computer algorithm based on the assay results of said panel of biomarkers; and/or e) determining the likely responsiveness of said subject to said treatment. In some embodiments, the SNPs may be assayed by sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

Further provided is a method of prognosticating responsiveness of a subject to a disease treatment using the companion diagnostic test disclosed herein. In some embodiments, the treatment may comprise a therapeutic regimen using a modulator of a retinoid X receptor (RXR), a retinoid acid receptor (RAR), a peroxisome proliferator-activated receptor (PPAR), a Liver X receptor (LXR), or a farnesoid X receptor (FXR), wherein the RXR modulator may be bexarotene. In some embodiments, the disease may be selected from the group consisting of small cell lung cancer, prostate cancer, breast cancer, cutaneous T-cell lymphoma, cancer prevention, metabolic syndrome, dermatologic disease, neurodegenerative disease and disorder. In some embodiments, the method may be used for selecting a patient who is most likely to benefit from the treatment or who is most likely to experience an adverse effect from the treatment.

In still another aspect, provided herein is a method of identifying a new biomarker using the panel of isolated biomarkers disclosed herein. In some embodiments, the new biomarker may be a DNA, a RNA, a polypeptide, a siRNA or another form of biomarker. Further provided herein is a method of identifying a drug target using the panel of isolated biomarkers disclosed herein. In some embodiments, the drug target may be identified based on a biological pathway related to a biomarker, wherein the biological pathway may be selected from the group consisting of reabsorption of bile acids, inward rectifier potassium channels, regulation of the actin cytoskeleton, nuclear localization, integrin receptors, sparc/osteonectin, cwcv and kazal-like domains proteoglycan (testican) 1, and polycomb group ring finger 5.

DETAILED DESCRIPTION OF THE INVENTION

Figure 1A:
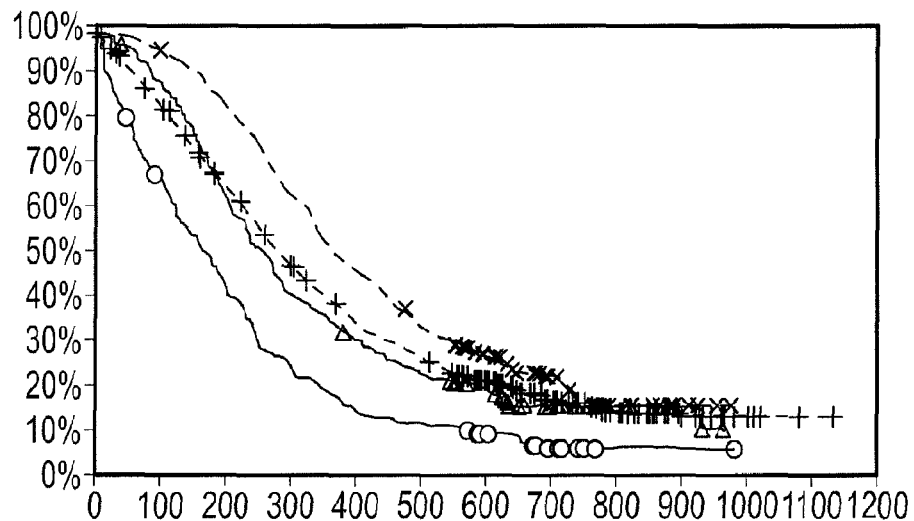
FIG. 1. Sub-population analysis and study design. A. Survival analysis of patients exhibiting different triglyceride levels following bexarotene treatment. The total number of patients (N=1213) included in the analysis were from both SPIRIT I and II studies, and they were divided into three subgroups based on the percentile of maximum triglyceride level they exhibited during the study. Therefore, 'HTG Lo' group includes those patients who experienced triglyceride levels up to 33% of the maximum triglyceride level in all treated patients, 'HTG Mid" includes the middle third (33% to 67%), and the 'HTG Hi' includes the patients exhibiting the highest levels of triglyceride (67% to maximum) during the treatment. Kaplan-Meier survival estimates in patients gave median survivals of 170 days, 263 days, and 371 days for these three groups, respectively. By this analysis, the control arm has a median survival of 284 days, which is significantly different from both the 'HTG Hi' group (log-rank p-value=0.003) and the 'HTG Lo' group (log-rank p-value <0.0001), but not from the 'HTG Mid' group (log-rank p-value=0.43). B. Overview of genome-wide association study design. In Stage I discovery phase, 150 samples (74 cases and 76 controls) were genotyped using the Affymetrix GeneChip 500K Mapping Array Set (Nsp array+ Sty array) containing 500,000 SNPs following the Affymetrix standard protocol. 255 SNPs were then selected for stage II study. In Stage II, 400 samples were individually genotyped using the 255 Sequenom iPLEX SNP assays, including 147 samples (minus one case and two controls) used in the Stage I for the Verification group and 253 new samples for the Replication group. In the Replication group, 129 samples were included from the patients with middle level of triglyceride percentile (HTG Mid).

The present invention describes genomic biomarkers that have been discovered to correlate with different responses (efficacy, adverse effect, and other end points) among patients receiving treatment regime including bexarotene, in treating diseases such as, non small cell lung cancer. The newly discovered biomarkers can be used in companion diagnostic tests which can help to predict drug responses and apply drugs only to those who will be benefited, or exclude those who might have adverse effects, by the treatment.

The present invention comprises a method of predicting responders to therapeutic regime which includes RXR modulator, such as bexarotene by using score generated by genotyping the genetic biomarkers and processing the results via computer algorithm.

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

B. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimens.

As used herein, a "pharmacogenomic biomarker" is an objective biomarker which correlates with a specific clinical drug response or susceptibility in a subject (see, e.g., McLeod et al., *Eur. J. Cancer* (1999) 35:1650-1652). It may be a biochemical biomarker, or a clinical sign or symptom. The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of DNA, RNA, or protein for specific tumor markers in a subject, a drug or course of treatment may be selected that is optimized for the treatment of the specific tumor likely to be present in the subject. Similarly, the presence or absence of a specific sequence mutation or polymorphism may correlate with drug response. The use of pharmacogenomic biomarkers therefore permits the application of the most appropriate treatment for each subject without having to administer the therapy.

As used herein, the term "polymorphic locus" refers to a region in a nucleic acid at which two or more alternative nucleotide sequences are observed in a significant number of nucleic acid samples from a population of individuals. A polymorphic locus may be a nucleotide sequence of two or more nucleotides, an inserted nucleotide or nucleotide sequence, a deleted nucleotide or nucleotide sequence, or a microsatellite, for example. A polymorphic locus that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic locus is often one nucleotide in length, which is referred to herein as a "single nucleotide polymorphism" or a "SNP." In some embodiments, the high-density genotyping may be conducted by using SNPs. In some embodiments, about 1,000-5,000,000 or more SNPs, may be used. In some embodiments, the high-density genotyping may be array-based. In some embodiments, the high-density genotyping may be conducted by using sequencing, such as high-throughput sequencing.

Where there are two, three, or four alternative nucleotide sequences at a polymorphic locus, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those individuals who possess two major alleles or two minor alleles are often referred to as being "homozygous" with respect to the polymorphism, and those individuals who possess one major allele and one minor allele are normally referred to as being "heterozygous" with respect to the polymorphism. Individuals who are homozygous with respect to one allele are sometimes predisposed to a different phenotype as compared to individuals who are heterozygous or homozygous with respect to another allele.

In genetic analysis that identifies one or more pharmacogenomic biomarkers, samples from individuals having different values in a relevant phenotype often are allelotyped and/or genotyped. The term "allelotype" as used herein refers to a process for determining the allele frequency for a polymorphic variant in pooled DNA samples from cases and controls. By pooling DNA from each group, an allele frequency for each locus in each group is calculated. These allele frequencies are then compared to one another.

A genotype or polymorphic variant may be expressed in terms of a "haplotype," which as used herein refers to a set of DNA variations, or polymorphisms, that tend to be inherited together. A haplotype can refer to a combination of alleles or to a set of SNPs found on the same chromosome. For example, two SNPs may exist within a gene where each SNP position includes a cytosine variation and an adenine variation. Certain individuals in a population may carry one allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "clinical sample" or "disease sample" and variations thereof refer to any sample obtained from a subject of interest that would be expected or is known to contain the cellular and/or molecular entity that is to be characterized.

The term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

"Plasma," or "blood plasma," as used herein, refers to the intravascular fluid part of extracellular fluid (all body fluid outside of cells). It is mostly water and contains dissolved proteins, glucose, clotting factors, mineral ions, hormones and carbon dioxide (plasma being the main medium for excretory product transportation). Blood plasma is prepared by spinning a tube of fresh blood containing an anticoagulant in a centrifuge until the blood cells fall to the bottom of the tube. The blood plasma is then poured or drawn off. "Blood serum" is blood plasma without fibrinogen or the other clotting factors (i.e., whole blood minus both the cells and the clotting factors).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "array" or "microarray", as used herein refers to an ordered arrangement of hybridizable array elements, such as polynucleotide probes (e.g., oligonucleotides), beads, or binding reagents (e.g., antibodies), on a substrate. The substrate can be a solid substrate, such as a glass or silica slide, a fiber optic binder, or a semi-solid substrate, such as nitrocellulose membrane. The nucleotide sequences can be DNA, RNA, or any permutations thereof.

As used herein, the term "phenotype" refers to a trait which can be compared between individuals, such as presence or absence of a condition, a visually observable difference in appearance between individuals, metabolic variations, physiological variations, variations in the function of biological molecules, and the like. A phenotype can be qualitative or quantitative. An example of a phenotype is responsiveness to a treatment, such as a drug.

"Responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) relief, to some extent, of one or more symptoms associated with the disorder; (7) increase in the length of disease-free presentation following treatment; (8) decreased mortality at a given point of time following treatment; and/or (9) lack of adverse effects following treatment. Responsiveness can also be assessed using any endpoint indicating side effect and/or toxicity to the patient.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "prediction" or "prognosis" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein, the term "output" refers to a value or score generated from a computer algorithm. The output may be generated based on assay results using the biomarkers disclosed herein as inputs to the computer algorithm. An "output" can be either quantitative or qualitative, and can be used for determining the likely responsiveness of a subject to a treatment in a companion diagnostic test.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

C. Biomarkers for Predicting Bexarotene Responsiveness

The present invention describes novel genomic biomarkers that correlate with the activity of RXR modulator, such as bexarotene. These biomarkers can be used to identify the patients who are most likely to benefit or experience adverse effect from bexarotene treatment.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. Preferably the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon).

In one aspect, the biomarkers of the invention are those provided in Table 2 and Table 3 and others in linkage disequilibrium with them:

```
rs7434820
                                    (SEQ ID NO: 1)
CGAGTGATAGGATGAGGCTAATGATA[C/T]AG
AGGGCGAAACATCTCCTCATTCA rs4572960
                                    (SEQ ID NO: 2)
CTCTCCAAAATAACTCTTCATGCACA[A/C/T]
TTTAGCTTACCTCTGAAAAACTACA rs10058324
                                    (SEQ ID NO: 3)
GCAGACAAAATAACATCTTTAACACA[A/G]CA
TCTCCGATAAAAAGATTCAAAAG rs10058324
                                    (SEQ ID NO: 4)
GCAGACAAAATAACATCTTTAACACA[A/G]CA
TCTCCGATAAAAAGATTCAAAAG
```

-continued

```
rs6997581
                                (SEQ ID NO: 5)
AAATGCACACCTAACGCACATTCCTG[C/T]GG
TCCAAGACAGCATGATTCCAGAG rs2631686
                                (SEQ ID NO: 6)
CAAGCAGCCCTTCCTGTCTTAGCCTA[C/T]AC
ATCATTACCTAATAAGCAAACCT rs1795505
                                (SEQ ID NO: 7)
CATCCATAAAATTACGTTTACAGTAG[C/G]TG
AAGGTACCAAATGGATCAGTCTC rs1184776
                                (SEQ ID NO: 8)
GAGAGGTTTATTCATGGATGGACTTC[C/T]TT
GTAGATGTTAGGTCAAAAAAAA rs7334509
                                (SEQ ID NO: 9)
TGCTCATAATGCTTACCATGCCATGG[A/G]TA
ATAGAGTTCTTTGCCATAGACCT rs6491738
                                (SEQ ID NO: 10)
ATCCATCTCCTTCCATCCTCAGACAT[C/T]GG
CACTCGTGGTTCTTGGGCCTTCA rs7333033
                                (SEQ ID NO: 11)
CAAGCCTTAATCCATGAGACAGATGT[A/C]TT
GGTTTTCTCACTTCTTTGGGTCA rs7338381
                                (SEQ ID NO: 12)
AATGTTTGCTCTAGATTCTTAAGGCC[A/G]CT
GTTCTTTTCAGCATGATTTTACT rs3916931
                                (SEQ ID NO: 13)
GAGGAGAATGAGGATCTGACACAAAG[A/T]AA
GATTATTATTTCCTGCAACAAGA rs1506011
                                (SEQ ID NO: 14)
ATGTAACATAGTGATGATTGAAACCC[A/G]AA
ATATAAATGAATGCCACATAATG
```

The invention includes individual biomarker and biomarker sets, which comprise more than one biomarker provided in Table 2 and Table 3. The biomarkers having predicting value for bexarotene treatment are not limited to the ones listed in Table 2 and Table 3. The invention also includes other biomarkers, e.g., SNPs, which have high correlation with the biomarkers listed in Table 2, and they could also be used to predict bexarotene responses by patients. For examples, those SNPs are in linkage disequilibrium with the SNPs provided in Table 2. Additional predicting SNPs might reside on genes related to the genes that SNPs listed in Table 2 are associated with. SNPs that are in linkage disequilibrium may be found in various public databases, e.g., HapMap.

In some embodiments, linkage disequilibrium (LD) refers to the co-inheritance of alleles (e.g., alternative nucleotides) at two or more different SNP sites at frequencies greater than would be expected from the separate frequencies of occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium". In contrast, LD refers to any non-random genetic association between allele(s) at two or more different SNP sites, which is generally due to the physical proximity of the two loci along a chromosome. See e.g., U.S. 2008/0299125.

In some embodiments, LD can occur when two or more SNPs sites are in close physical proximity to each other on a given chromosome and therefore alleles at these SNP sites will tend to remain unseparated for multiple generations with the consequence that a particular nucleotide (allele) at one SNP site will show a non-random association with a particular nucleotide (allele) at a different SNP site located nearby. Hence, genotyping one of the SNP sites will give almost the same information as genotyping the other SNP site that is in LD. See e.g., U.S. 2008/0299125.

In some embodiments, for diagnostic purposes, if a particular SNP site is found to be useful for diagnosing, then the skilled artisan would recognize that other SNP sites which are in LD with this SNP site would also be useful for diagnosing the condition. Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome. See e.g., U.S. 2008/0299125.

D. Applications of the Biomarkers

Information generated from genomic biomarkers described herein can be used to determine appropriate dosage and/or treatment regimens for an individual with non small cell lung cancer. This knowledge, when applied to dosing or drug selection, can avoid adverse reactions or therapeutic failure and thus enhance therapeutic efficiency when administering a therapeutic composition, such as bexarotene.

The biomarkers disclosed herein and their associated SNPs or genes could also be used to predict patient's responses to treatment of other diseases or conditions besides non small cell lung cancer. These diseases include, but are not limited to, prostate cancer, breast cancer, cutaneous T-cell lymphoma, cancer prevention, metabolic syndrome, dermatologic disease, neurodegenerative diseases and disorders such as Alzheimer's disease, which was shown to respond to bexarotene in a mouse model (30).

The biomarkers disclosed herein and their associated SNPs or genes could also be used to predict patient's responses to treatment of PPARγ and/or RXR related diseases and disorders (see, e.g., PCT Publication No. WO 2011/006157). PPARγ and/or RXR related diseases and disorders can include, but are not limited to, neurodegenerative diseases and disorders, diseases and disorder resulting from trauma and injury, and/or an inflammatory component as well as dermatological diseases and disorders with or without an inflammatory component.

Neurodegenerative disorders include, but are not limited to, Alzheimer's, Parkinson's, Huntington's Disease, as well as neural diseases and conditions with an inflammatory components, including, but not limited to, central nervous system injuries, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HW/AIDs dementia complex, and bacterial, parasitic, fungal, and viral meningitis and encephalitis.

In other aspects, the biomarkers disclosed herein and their associated SNPs or genes could also be used to predict patient's responses to treatment of cystic fibrosis (CF) and CF-related disease(s) and disorder(s) (e.g., variant cystic fibrosis and non-CF bronchiectasis inflammatory responses), and inflammatory responses associate with associated with cystic fibrosis-related disease(s) or disorder(s). In still further aspects, the biomarkers disclosed herein and their associated SNPs or genes could also be used to predict patient's responses to treatment of dermatological diseases and/or disorders where lipid PPARγ-regulated gene expression is decreased (e.g., LPP).

The treatments of the present invention can include the use of RXR agonist alone or in combination with a PPARγ agonist (and optionally a LXR agonist) to suppress, inhibit, or mitigate a diverse range of PPARγ and/or RXR related diseases as described above and/or inflammatory responses associated with the PPARγ and/or RXR related diseases.

Pharmacogenomics involves tailoring a treatment for a subject according to the subject's genotype as a particular treatment regimen may exert a differential effect depending upon the subject's genotype. For example, based upon the outcome of a prognostic test, a clinician or physician may target pertinent information and preventative or therapeutic treatments to a subject who would be benefited by the information or treatment and avoid directing such information and treatments to a subject who would not be benefited (e.g., the treatment has no therapeutic effect and/or the subject experiences adverse side effects). Information generated from pharmacogenomic biomarkers using a method described herein can be used to determine appropriate dosage and treatment regimens for an individual. This knowledge, when applied to dosing or drug selection, can avoid adverse reactions or therapeutic failure and thus enhance therapeutic efficiency when administering a therapeutic composition. In some embodiments, the pharmacogenomic biomarker may be used to develop a companion diagnostic test.

Therefore, in a further aspect, provided herein is a companion diagnostic test using the biomarkers disclosed herein. For example, in one embodiment, a physician or clinician may consider applying knowledge obtained in biomarkers using a method described herein, when determining whether to administer a pharmaceutical composition to a subject. In another embodiment, a physician or clinician may consider applying such knowledge when determining the dosage, e.g., amount per treatment or frequency of treatments, of a treatment, administered to a patient.

The invention provides methods for assessing or aiding assessment of responsiveness of a subject to treatment. The invention also provides methods for predicting responsiveness or monitoring treatment/responsiveness to a treatment in a subject. The invention provides methods for selecting a subject for treatment and treating the subject. In some embodiments, the methods comprise assessing one or more pharmacogenomic biomarkers in a sample obtained from the subject; and predicting, assessing, or aiding assessment of responsiveness of the subject to a treatment based on the genotype of said one or more pharmacogenomic biomarkers. In some embodiments, the responsiveness is predicted or assessed by classifying the subject using an algorithm such as SVM, logistic regression, or K-nearest neighbors analysis.

The following is an example of a pharmacogenomic embodiment. A particular treatment regimen can exert a differential effect depending upon the subject's genotype. Where a candidate therapeutic exhibits a significant interaction with a major allele and a comparatively weak interaction with a minor allele (e.g., an order of magnitude or greater difference in the interaction), such a therapeutic typically would not be administered to a subject genotyped as being homozygous for the minor allele, and sometimes not administered to a subject genotyped as being heterozygous for the minor allele. In another example, where a candidate therapeutic is not significantly toxic when administered to subjects who are homozygous for a major allele but is comparatively toxic when administered to subjects heterozygous or homozygous for a minor allele, the candidate therapeutic is not typically administered to subjects who are genotyped as being heterozygous or homozygous with respect to the minor allele.

The methods described herein are applicable to pharmacogenomic methods for preventing, alleviating or treating conditions such as metabolic disorders, cardiovascular diseases, cancers, etc. For example, a nucleic acid sample from an individual may be subjected to a prognostic test described herein. Where one or more polymorphic variations associated with increased risk of type II diabetes are identified in a subject, information for preventing or treating type II diabetes and/or one or more type II diabetes treatment regimens then may be prescribed to that subject.

In certain embodiments, a treatment regimen is specifically prescribed and/or administered to individuals who will most benefit from it based upon their likelihood of responding to a treatment regimen assessed by the methods described herein. Thus, provided are methods for identifying a subject with a high likelihood of responding to a treatment regimen and then prescribing such treatment regimen to individuals identified as having a high likelihood of responding. Thus, certain embodiments are directed to a method for treating a subject, which comprises: detecting the presence or absence of a pharmacogenomic biomarker associated with responsiveness to a treatment regimen in a nucleotide sequence set forth herein in a nucleic acid sample from a subject, and prescribing or administering the treatment regimen to a subject from whom the sample originated where the presence of a pharmacogenomic biomarker associated with responsiveness to the treatment regimen is detected in the nucleotide sequence.

The treatment sometimes is preventative (e.g., is prescribed or administered to reduce the probability that a disease condition arises or progresses), sometimes is therapeutic, and sometimes delays, alleviates or halts the progression of a disease condition. Any known preventative or therapeutic treatment for alleviating or preventing the occurrence of a disorder may be prescribed and/or administered.

Pharmacogenomics methods also may be used to analyze and predict a response to a drug. For example, if pharmacogenomics analysis indicates a likelihood that an individual will respond positively to a treatment with a particular drug, the drug may be administered to the individual. Conversely, if the analysis indicates that an individual is likely to respond negatively to treatment with a particular drug, an alternative course of treatment may be prescribed. The response to a therapeutic treatment can be predicted in a background study in which subjects in any of the following populations are genotyped: a population that responds favorably to a treatment regimen, a population that does not respond significantly to a treatment regimen, and a population that responds adversely to a treatment regiment (e.g., exhibits one or more side effects). These populations are provided as examples and other populations and subpopulations may be analyzed. Based upon the results of these analyses, a subject is genotyped to predict whether he or she will respond favorably to a treatment regimen, not respond significantly to a treatment regimen, or respond adversely to a treatment regimen.

The comparisons and/or calculations for predicting, assessing or aiding assessment can be carried out in any convenient manner appropriate to the type of measured value and/or reference value for the pharmacogenomic biomarkers at issue. The process of comparing or calculating may be manual or it may be automatic (such as by a machine including computer-based machine). As will be apparent to those of skill in the art, replicate genotyping may be taken for the pharmacogenomic biomarkers.

Also provided herein is a method of prognosticating responsiveness of a subject to a treatment using the companion diagnostic test disclosed herein. The tests described herein also are applicable to clinical drug trials. In some embodiments, the pharmacogenomic biomarkers can be used to stratify or select a subject population for a clinical trial. The pharmacogenomic biomarkers can, in some embodiments, be used to stratify individuals that may exhibit a toxic response to a treatment from those that will not. In other embodiments, the pharmacogenomic biomarkers can be used to separate those that will be non-responders from those who will be responders. The pharmacogenomic biomarkers described herein can be used in pharmacogenomic-based design and in managing the conduct of a clinical trial.

Thus, another embodiment is a method of selecting an individual for inclusion in a clinical trial of a treatment or drug comprising the steps of: (a) obtaining a nucleic acid sample from an individual; (b) determining the identity of a polymorphic variation which is associated with a positive response to the treatment or the drug, or at least one polymorphic variation which is associated with a negative response to the treatment or the drug in the nucleic acid sample, and (c) including the individual in the clinical trial if the nucleic acid sample contains said polymorphic variation associated with a positive response to the treatment or the drug or if the nucleic acid sample lacks said polymorphic variation associated with a negative response to the treatment or the drug. In addition, the methods described herein for selecting an individual for inclusion in a clinical trial of a treatment or drug encompass methods with any further limitation described in this disclosure, or those following, specified alone or in any combination. The including step (c) optionally comprises administering the drug or the treatment to the individual if the nucleic acid sample contains the polymorphic variation associated with a positive response to the treatment or the drug and the nucleic acid sample lacks said biallelic marker associated with a negative response to the treatment or the drug.

E. Additional Biomarkers or Drug Targets

Also provided is a method for identifying polymorphic variants proximal to the biomarkers disclosed herein. In some embodiments, the proximal polymorphic variant identified sometimes is a publicly disclosed polymorphic variant, which for example, sometimes is published in a publicly available database. In other embodiments, the polymorphic variant identified is not publicly disclosed and is discovered using a known method, including, but not limited to, sequencing a region surrounding the identified pharmacogenomic biomarker in a group of nucleic samples. Thus, multiple polymorphic variants proximal to a biomarker are identified using this method.

The proximal polymorphic variant often is identified in a region surrounding the biomarker. In certain embodiments, this surrounding region is about 50 kb flanking the biomarker (e.g., about 50 kb 5' of the first polymorphic variant and about 50 kb 3' of the first polymorphic variant), and the region sometimes is composed of shorter flanking sequences, such as flanking sequences of about 40 kb, about 30 kb, about 25 kb, about 20 kb, about 15 kb, about 10 kb, about 7 kb, about 5 kb, or about 2 kb 5' and 3' of the biomarker. In other embodiments, the region is composed of longer flanking sequences, such as flanking sequences of about 55 kb, about 60 kb, about 65 kb, about 70 kb, about 75 kb, about 80 kb, about 85 kb, about 90 kb, about 95 kb, or about 100 kb 5' and 3' of the biomarker.

In certain embodiments, polymorphic variants are identified iteratively. For example, a first proximal polymorphic variant is identified using the methods described above and then another polymorphic variant proximal to the first proximal polymorphic variant is identified (e.g., publicly disclosed or discovered) and the presence or absence of an association of one or more other polymorphic variants proximal to the first proximal polymorphic variant is determined.

The methods described herein are useful for identifying or discovering additional polymorphic variants that may be used to further characterize a gene, region or loci associated with a condition, a disease, or a disorder. For example, allelotyping or genotyping data from the additional polymorphic variants may be used to identify a functional mutation or a region of linkage disequilibrium. In certain embodiments, polymorphic variants identified or discovered within a region comprising the biomarker are genotyped, and it can be determined whether those polymorphic variants are in linkage disequilibrium with the biomarker. The size of the region in linkage disequilibrium with the biomarker also can be assessed using these genotyping methods. Thus, provided herein are methods for determining whether a polymorphic variant is in linkage disequilibrium with a biomarker, and such information can be used in prognosis/diagnosis methods described herein.

Additionally, genes may be identified that are in proximity to the biomarkers, and their functions analyzed. Genes with functions that are directly or indirectly related to the relevant phenotype, or other genes in the same cellular pathway, may be targets for further analysis with the relevant phenotype, and new biomarkers may be identified.

Further provided herein is a method of developing novel therapeutic agents and/or identifying a novel drug target using the biomarkers disclosed herein. In some embodiments, the biomarkers and their associated SNPs or genes could gain insight of the underlying biological pathways or mechanisms underlying the studied phenotypes, such as efficacy, adverse effect, or other endpoints.

For instance, clinical applications of retinoids in general, and RXR agonists as well, have been in part limited by associated undesirable side-effects, e.g., the elevation of serum triglycerides. Although the induction of hypertriglyceridemia by RXR agonists has been known for a long time, the molecular mechanism underlying this phenomenon remains elusive. One of the associated loci identified from this study, SLC10A2, is an attractive candidate that might be involved in rexinoid-induced hypertriglyceridemia. SLC10A2 is a gene responsible for reabsorption of bile acids from the small intestine. Bile acids are known to affect serum triglyceride levels (15-18), and as the major component for bile acid uptake, the activity of SLC10A2 is closely related to triglyceride levels (19, 20). Moreover, SLC10A2 is known to be regulated by RXR at the transcriptional level, probably through forming a heterodimer with PPARα; a nuclear receptor known to participate in lipid metabolism (21, 22). Thus the discoveries made in this invention might facilitate developing assays based on SLC10A2 or other genes involved in related pathways, which could lead to design a new generation of RXR agonist with reduced or minimal adverse affect like hypertriglyceridemia.

Another associated locus identified in this invention, rs7334509, is located near LCP1, which is also called L-Plastin. Plastins are a family of actin-binding proteins that are conserved throughout eukaryote evolution and expressed in most tissues of higher eukaryotes. These proteins share the unique property of cross-linking actin filaments into tight bundles, and they are primarily involved in regulation of the actin cytoskeleton. L-Plastin is predominantly expressed in hematopoietic cells, but has also been shown to be expressed in most human cancer cells and might be involved in DNA repair, tumor cell migration and invasion (23, 24). In our microarray study, expression of LCP1 in the paclitaxel-resistant MDA-PR cell line was significantly up-regulated by a combination of bexarotene and paclitaxel treatment. This result implies that LCP1 might be involved in the antitumor action exerted by bexarotene. Recent studies have found both actin and tubulin to be involved in tumor cell-resistance to chemotherapy (25-27). Thus, the LCP1 or related genes may become a novel drug target for antitumor agent.

F. Reagents and Kits

The present invention contemplates the preparation of kits, chips, devices, or assays for use in accordance with the present invention. Such an assay, chip, device, or a kit may comprise a plurality of primers or probes to detect genetic signature of SNPs such the ones listed in Table 2 and Table 3. Such methods can include instruments and instructions that a subject can use to obtain a sample, e.g., of buccal cells or blood, without the aid of a health care provider.

Figure 4:
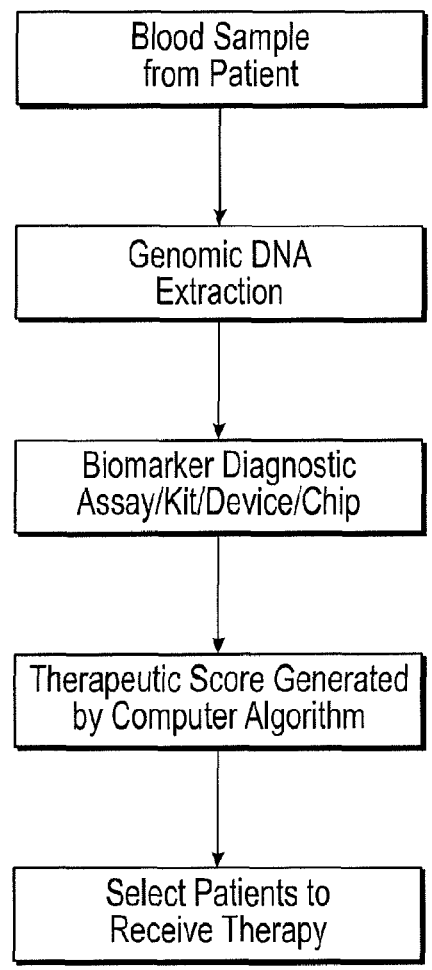
FIG. 4. The method of determining whether a human subject should receive therapy using predicting genomic biomarkers.

The invention also contemplates the development of computer algorithm which will convert the test results generated from the measurement of the genomic biomarkers into an output, e.g., a score, (See e.g., FIG. 4), which will be used to determine in whether an individual should receive the therapeutic invention, such as bexarotene treatment.

Diagnostic kits based on the biomarkers described above might be developed, and they can be used to predict individual's response to the corresponding drug. Such test kits can include devices and instructions that a subject can use to obtain a sample, e.g., of buccal cells or blood, without the aid of a health care provider.

For use in the applications described or suggested above, kits or articles of manufacture are also provided by the invention. Such kits may comprise at least one reagent specific for genotyping a biomarker described herein, and may further include instructions for carrying out a method described herein.

In some embodiments, the invention provides compositions and kits comprising primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of polynucleotides in a sample and as a means for detecting cell expressing proteins encoded by the polynucleotides. As will be understood by the skilled artisan, a great many different primers and probes may be prepared based on the sequences provided herein and used effectively to amplify, clone and/or determine the presence and/or levels of genomic DNAs.

In some embodiments, the kit may comprise reagents for detecting presence of polypeptides. Such reagents may be antibodies or other binding molecules that specifically bind to a polypeptide. In some embodiments, such antibodies or binding molecules may be capable of distinguishing a structural variation to the polypeptide as a result of polymorphism, and thus may be used for genotyping. The antibodies or binding molecules may be labeled with a detectable marker, such as, for example, a radioisotope, fluorescent compound, bioluminescent compound, a chemiluminescent compound, metal chelator or enzyme. Other reagents for performing binding assays, such as ELISA, may be included in the kit.

In some embodiments, the kits comprise reagents for genotyping at least two, at least three, at least five, at least ten, or more biomarkers. In some embodiments, the kits may further comprise a surface or substrate (such as a microarray) for capture probes for detecting of amplified nucleic acids.

The kits may further comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a biomarker. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kit can further comprise a set of instructions and materials for preparing a tissue or cell sample and preparing nucleic acids (such as genomic DNA) from the sample.

The invention provides a variety of compositions suitable for use in performing methods of the invention, which may be used in kits. For example, the invention provides surfaces, such as arrays that can be used in such methods. In some embodiments, an array of the invention comprises individual or collections of nucleic acid molecules useful for detecting pharmacogenomic biomarkers of the invention. For instance, an array of the invention may comprises a series of discretely placed individual nucleic acid oligonucleotides or sets of nucleic acid oligonucleotide combinations that are hybridizable to a sample comprising target nucleic acids, whereby such hybridization is indicative of genotypes of the pharmacogenomic biomarkers of the invention.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into nucleic acid molecules that are synthesized. The synthesized product is then contacted with a solid substrate, such as a glass slide, which is coated with an aldehyde or another reactive group which will form a covalent link with the reactive group that is on the amplified product and become covalently attached to the glass slide. Other methods, such as those using amino propryl silica surface chemistry are also known in the art, as disclosed at world wide web at cmt.corning.com and cmgm.stanford.edu/pbrownl.

Attachment of groups to oligonucleotides which could be later converted to reactive groups is also possible using methods known in the art. Any attachment to nucleotides of oligonucleotides will become part of oligonucleotide, which could then be attached to the solid surface of the microarray. Amplified nucleic acids can be further modified, such as through cleavage into fragments or by attachment of detectable labels, prior to or following attachment to the solid substrate, as required and/or permitted by the techniques used.

G. Example

The following example is offered to illustrate but not to limit the invention.

Example 1

Identification of Polymorphisms Associated with Hypertriglyceridemia and Prolonged Survival Induced by Bexarotene in Treating Non-Small Cell Lung Cancer Materials and Methods Patients. Among patients enrolled in the SPIRIT I and II trials and treated with bexarotene, plasma samples from 403 individuals were available. The clinical characteristics of these subjects are provided in Table I. The cases were defined as those whose triglyceride level percentiles were higher than 62 (upper third HTG Hi), and the controls were those whose triglyceride level percentiles were lower than 31 (lower third or HTG Lo). Those patients whose plasma triglyceride levels were between 31 and 62 were categorized into a middle group (HTG Mid).

DNA preparation. DNA was extracted from plasma samples with the QIAGEN QIAamp MinElute Virus Spin Kit (Valencia, Calif., USA). DNA samples were amplified using the Amersham Bioscience GenomiPhi DNA Amplification Kit (Piscataway, N.J., USA).

Figure 1B:
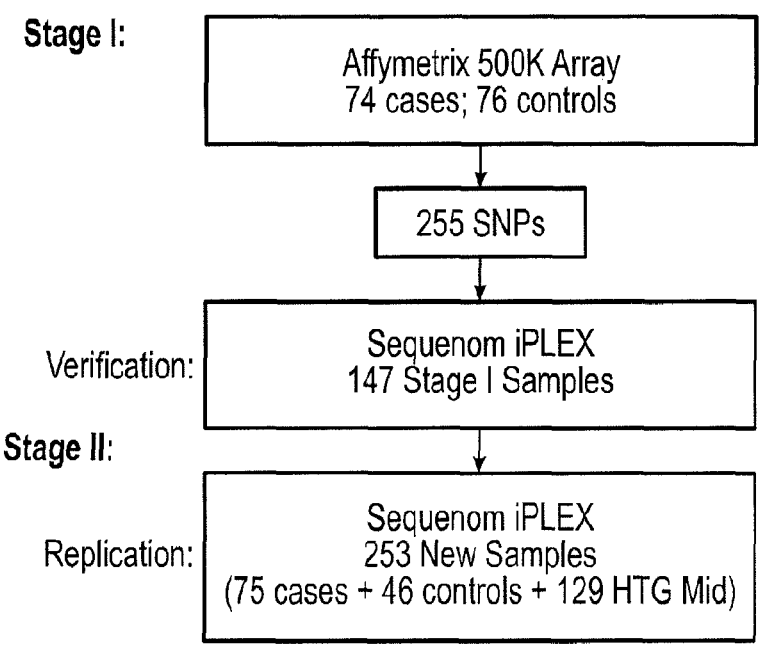

SNP genotyping and data analysis. In Stage I (FIG. 1B), 150 samples were genotyped using the Affymetrix GeneChip 500K Mapping Array Set containing 500,000 SNPs following Affymetrix standard protocol (Santa Clara, Calif., USA). From the genome-wide scan results, 255 SNPs were selected for Stage II study using Sequenom iPLEX™ assays (Sequenom, San Diego, Calif., USA). These assays were used to genotype 400 DNA samples from the SPIRIT trials. Among them, 147 samples out of the 150 samples used in Stage I were selected as the verification group, and the other 253 samples were used as the replication group (FIG. 1B). Final genotype calls were generated by Sequenom Typer Analyzer from the MassARRAY Typer suite (Sequenom, San Diego, Calif., USA). After removing the samples having call rates lower than 50%, 385 samples remained (141 samples in the verification group and 244 in the replication group). The case control analysis of associated SNPs was carried out using chi-square test based on differences in allele counts between cases and controls. Subsequently, the level of triglyceride percentile was used as a quantitative trait and association analysis was performed by least squares regression using PLINK program (12).

Paclitaxel-resistant MDA-MB-231 cells and resensitization with bexarotene treatment. The human breast cancer cell line MDA-MB-231 was obtained from the American Type Culture Collection (Manassas, Va., USA), and MDA-MB-231 cells were routinely cultured in RPMI-1640 supplemented with 10% fetal bovine serum and 2 mM glutamine in 5% $CO_2$. Bexarotene was synthesized at Ligand Pharmaceuticals Inc. (San Diego, Calif., USA), and paclitaxel was purchased from Sigma Chemicals (St. Louis, Mo., USA). The protocol for establishment of paclitaxel-resistant MDA-MB-231 cells and resensitization to paclitaxel by bexarotene treatment was described previously (5). Briefly, MDA-MB-231 cells were exposed to regimens on a 10-day cycle: a 3-day treatment with 30 nM paclitaxel followed by a 7-day exposure to control medium. Paclitaxel-resistant MDA-MB-231 cells (MDA-PR) were established within 8 cycles of such treatment (3 days on and 7 days off; total of 80 days). These MDA-PR cells were then treated with the combination of 30 nM paclitaxel (3 days on and 7 days off) in the absence or presence of 1 µM Targretin (10 days on) in a new 10-day cycle for 3 months. MDA-PR cells thus treated became re-sensitized to paclitaxel. Meanwhile, the regimen including paclitaxel alone had no effect on the growth of MDA-PR cells.

RNA microarray. RNA was extracted from parent and paclitaxel-resistant MDA-MB-231 breast cancer cells treated with vehicle control, paclitaxel alone or with bexarotene as described in previous section (Paclitaxel resistant MDA-MB-231 cells and resensitization with bexarotene treatment). All RNA samples had satisfactory 28S/18S ratio when analyzed with 2100 Bioanalyzer (Agilent, Palo Alto, Calif., USA). A single probe was prepared for each RNA sample and hybridized to a single array using the standard protocol and reagents supplied by Affymetrix, and the probe was then hybridized to Affymetrix HG-U133A array (22,283 probe sets).

Results

Plasma samples from 403 patients who participated in the SPIRIT I and II trials were available for our study, and they were divided into high, middle and low groups based on their percentile of maximum triglyceride level exhibited during bexarotene treatment (Table 1). This grouping strategy mimicked the grouping method illustrated in the survival analysis reported earlier (9, 10) and shown in FIG. 1A, in which distinct survival results were observed when patients were divided into three groups based on their absolute triglyceride levels reached following bexarotene treatment.

In Stage I, 74 samples were randomly selected from the high HTG (case) and 76 samples were selected from the low HTG (control) subgroups, and they were genotyped with Affymetrix 500K SNP array (FIG. 1B). From the initial genome-wide scan, 255 SNPs were selected for the Stage II genotyping study using all except 3 available clinical samples with Sequenom iPLEX assays. Among the 400 samples, 147 samples (73 cases+74 controls) were selected as the verification group, and the other 253 samples (76 cases+48 controls+129 HTG Mid) were termed the replication group (FIG. 1B). To perform association analysis, p-values were first calculated based on the allelic frequency differences between cases and controls (Table 2). Genotypic tests were also performed using triglyceride percentile as the quantitative trait in the three groups (Table 3). For this analysis, individuals with the middle level of triglyceride percentile were included in the replication group. Significant associations were declared for SNPs with p-values ≤0.05. By combining these two approaches and criteria for significance, 14 SNPs showing significant associations with triglyceride level were found (Table 2, 3).

Figure 2:
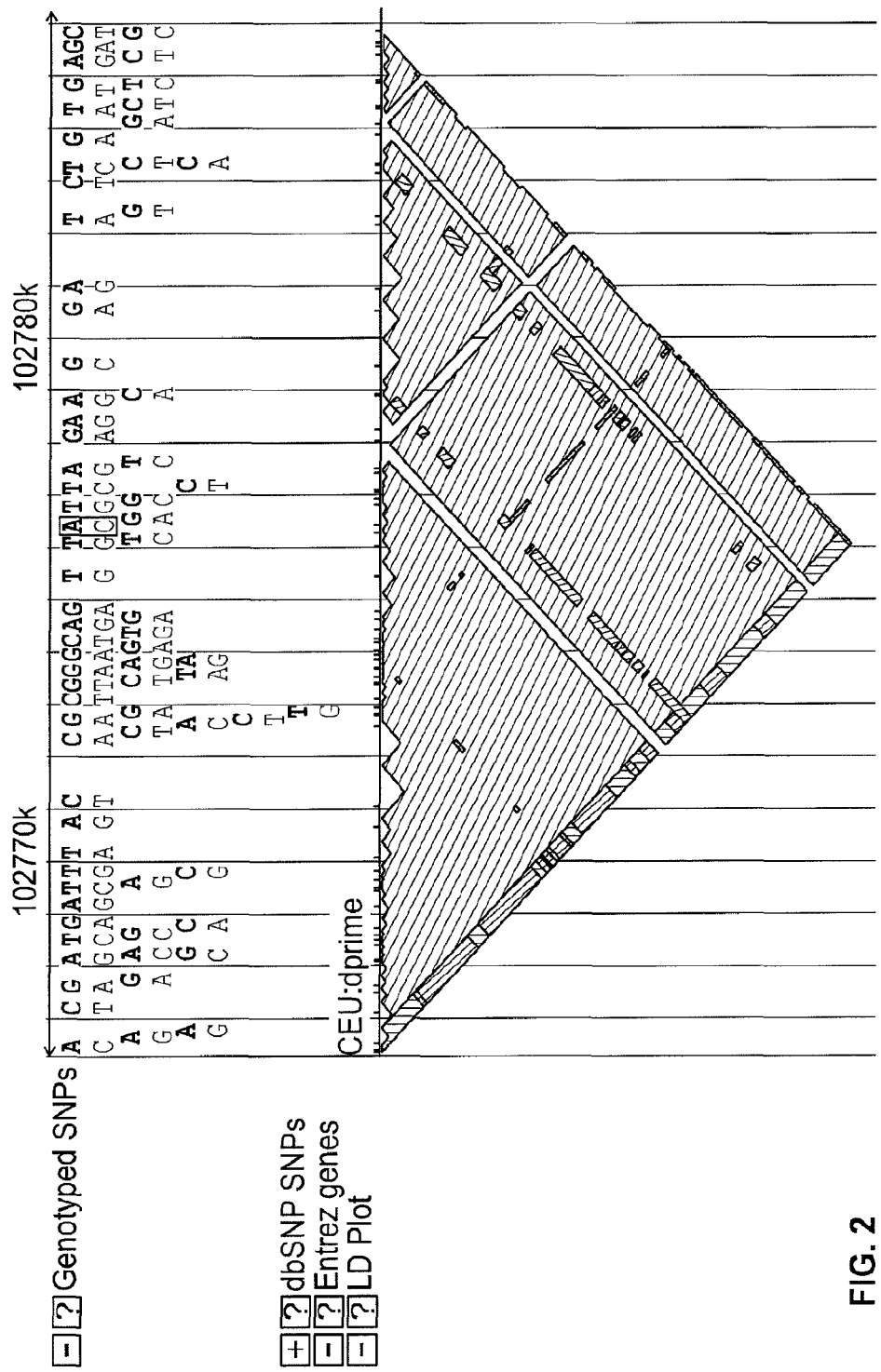
FIG. 2. Regional plot of the associated region at SLC10A2. The significant association at a locus near SLC10A2 was identified using Sequenom iPLEX. The graph is generated from hapmap, and the ruler at the top represents the physical position on Chr13. There are four SNPs (marked by four purple circles) from this region showing significant association with bexarotene-induced hypertriglyceridemia, and they are in strong LD block which is displayed in red triangles or blocks. The LD plot was generated using hapmap website's default settings, the dark red represents d-prime from CEU larger than 1.

Associated loci. The 14 SNPs with significant associations with hypertriglyceridemia (Table 2, 3) are located on 9 loci. Four significantly associated SNPs are located within the same linkage disequilibrium (LD) block on chromosome 13 (FIG. 2). This region lies approximately 200 kb upstream of SLC10A2, a gene responsible for reabsorption of bile acids from the small intestine. The second region with multiple SNPs showing a strong association is located on chromosome 12, where rs1795505 and rs1184776 are only about 5000 nucleotides apart. Both SNPs lie in the intron region of Lin-7 homolog A (Lin7A), but this region is in an LD block containing the 2nd and 3rd exons of the Lin7A gene.

Figure 3A:
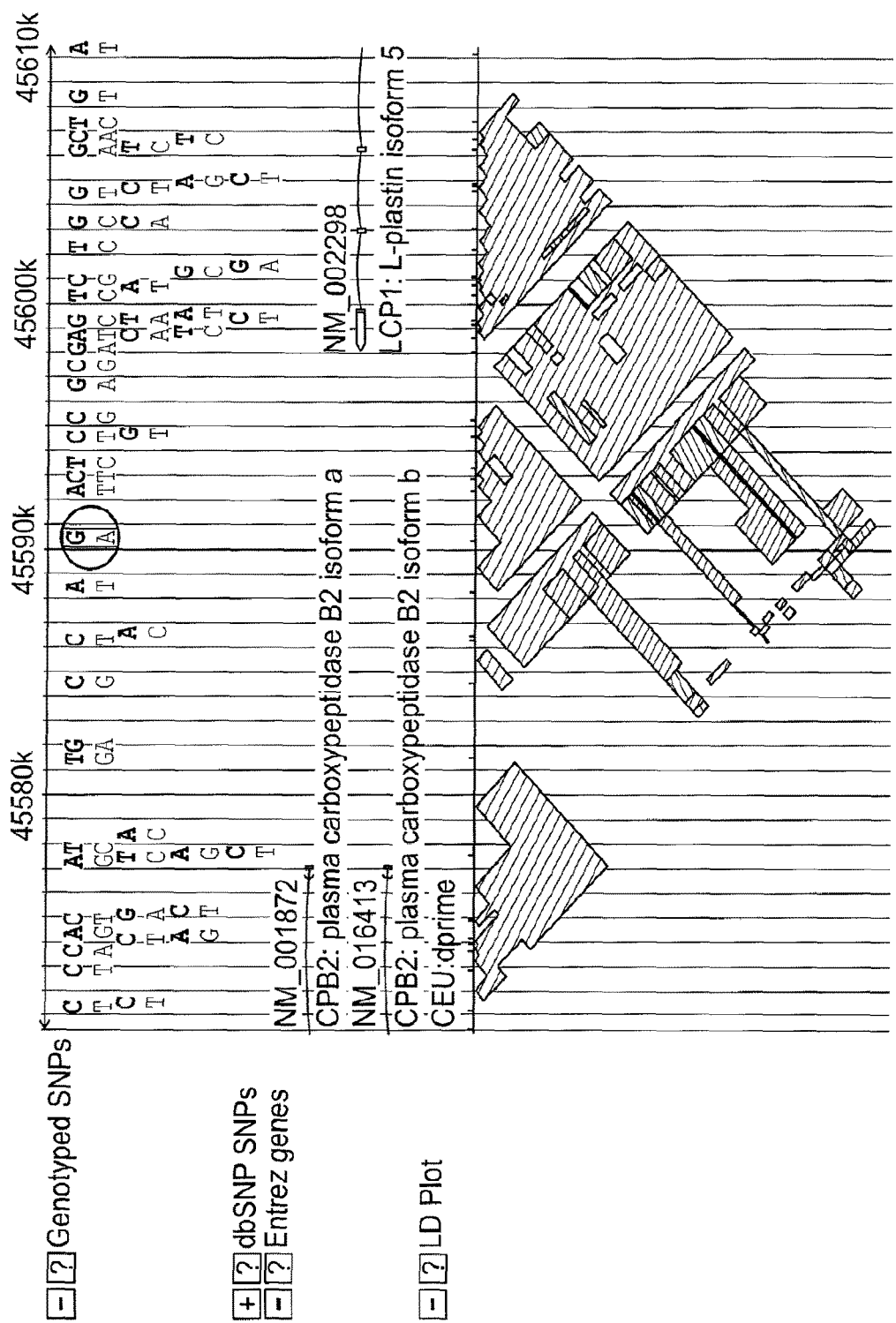
FIG. 3. Associated and functional analysis of LCP1. A. Physical location of rs7334509 on Chr13 and its associated genes. The number along the ruler at the top indicates the physical position on Chr13, and SNPs in this region are shown in two-letter code corresponding to the two alleles of each SNP. rs7334509 is highlighted by a purple circle. The two known genes located in this region, CPB2 and LCP1, are also displayed. The introns of the genes are shown by black curved lines, and exons are illustrated by a box, with coding region shown in yellow and untranslated regions shown in grey. The LD plot was generated using hapmap website's default settings, the dark red represents d-prime from CEU larger than 1. B. Regulation of LCP1 expression in MDA-MB-231 (MDA) cells and its derivative paclitaxel-resistant MDA-PR cells. LCP1 expression data was obtained from the microarray experiment using four groups of samples: i) MDA parental cells; ii) MDA derived cells resistant to paclitaxel (MDA-PR); iii) MDA-PR cells treated with 30 nM paclitaxel (3 days on, 7 days off) for 3 months; iv) MDA-PR cells treated with 30 nM paclitaxel/1 µM bexarotene (3 days both, 7 days only bexarotene) for 3 months. Each group had four replicates and different groups are shown in a different shade of blue color. The LCP1 expression signal of each sample is labeled at the end of the bar graph. Comparing to MDA parental cells, LCP1 expression in MDA-PR is 4.3-fold lower with p-value=$1.50 \times 10^{-7}$. LCP1 expression was significantly up-regulated by 3.8-fold in MDA-PR cells treated with paclitaxel and bexarotene compared to MDA-PR cells (p-value=$6.86 \times 10^{-6}$).
Figure 3B:
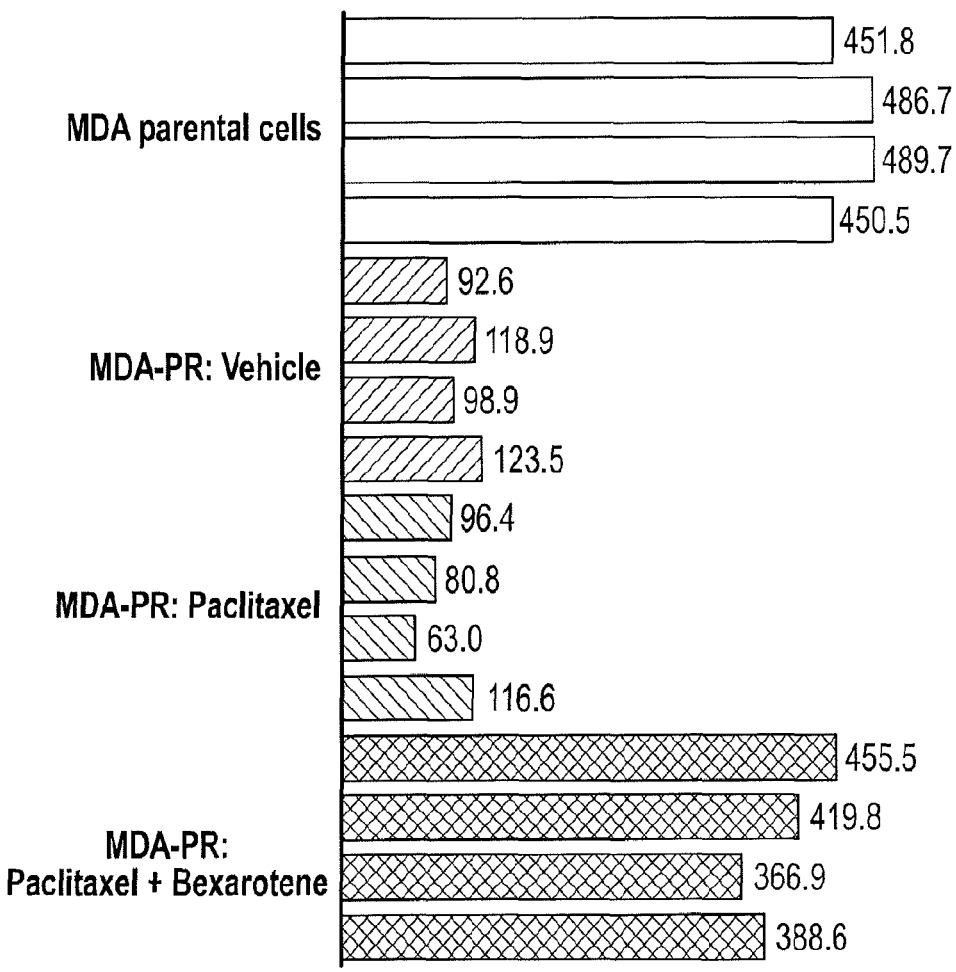

Another associated SNP, rs7334509, lies between LCP1 and carboxypeptidase B2 (CBP2), and resides in an LD block containing the 3' half of the LCP1 (FIG. 3A). Bexarotene has been shown to resensitize breast cancer cells which had become chemo resistant after prolonged treatment with chemotherapy agents, such as paclitaxel (5). Examination of gene expression data from the microarray study with MDA-PR cells resistant to paclitaxel revealed that LCP1, which lies close to rs7334509, was up-regulated by co-treatment with bexarotene (FIG. 3B). In the microarray study, expression of LCP1 was significantly reduced in the paclitaxel resistant MDA-PR cell line compared to its parent cell line. In MDA-PR cells treated with bexarotene and paclitaxel, LCP1 expression was significantly up-regulated, to about the same level as that in parental MDA-MB-231 cells (FIG. 3B). However, treatment with paclitaxel alone had no effect on the expression of LCP1.

For the rest of the significant SNPs, three have p-values <5 ×$10^{-7}$ (rs6997581,p=3.16×$10^{-10}$; rs1506011, p=3.88 ×$10^{-8}$; rs4572960, p=1.59 ×$10^{-7}$) (Table 2). The most strongly associated SNP, rs6997581, is distantly surrounded by two genes, 400 kb to CSMD1(CUB and Sushi multiple domains 1) and 900 kb to MCPH1 (microcephaly, primary autosomal recessive 1). Rs4572960 and the closely located rs10058324 (1.59 ×$10^{-5}$) are about 70 kb from each other and in weak LD, with D'=0.8. There are two genes, PELO (Pelota homolog) and ITGA1(integrin alpha 1), which are located 500 kb away from this locus. PELO encodes a protein which contains a conserved nuclear localization signal, and ITGA1 encodes the alpha 1 subunit of integrin receptors. No known gene was found to reside in the vicinity of rs1506011. The remaining three significant SNPs, rs7434820 (FLJ46481), rs1051853 (sparc/osteonectin, cwcv and kazal-like domains proteoglycan (testican) 1 (SPOCK1)), and rs2631686 (polycomb group ring finger 5(PCGF5)) exhibit modest association with hypertriglyceridemia.

RXR is able to form heterodimers with a number of nuclear receptors, such as retinoid acid receptors, PPAR, LXR, and FXR, and is a pleiotropic regulator involved in many biological pathways. With the development of RXR-specific agonists, such as bexarotene, tremendous potential exists to benefit many critical therapeutic areas, including metabolic syndrome, dermatologic disease, treatment of tumors and cancer prevention (13, 14). Clinical applications of retinoids in general, and RXR agonists as well, have been in part limited by associated undesirable side-effects, e.g., the elevation of serum triglycerides. Although the induction of hypertriglyceridemia by RXR agonists has been known for a long time, the molecular mechanism underlying this phenomenon remains elusive. One of the associated loci identified from this study, SLC10A2, is an attractive candidate that might be involved in rexinoid-induced hypertriglyceridemia. SLC10A2 is a gene responsible for reabsorption of bile acids from the small intestine. Bile acids are known to affect serum triglyceride levels (15-18), and as the major component for bile acid uptake, the activity of SLC10A2 is closely related to triglyceride levels (19, 20). Moreover, SLC10A2 is known to be regulated by RXR at the transcriptional level, probably through forming a heterodimer with PPARα, a nuclear receptor known to participate in lipid metabolism (21, 22). Down-stream conversion of triglycerides into fatty acids also generates signaling molecules that activate a number of nuclear receptors, many of which form heterodimer partners with the RXR receptors, potentially triggering other cellular mechanisms controlling cancer cell growth.

This study also allows insight into antitumor activity of the bexarotene due to the correlation between survival and highly elevated triglyceride levels. One associated locus, rs7334509, is located near LCP1, which is also called L-Plastin. Plastins are a family of actin-binding proteins that are conserved throughout eukaryote evolution and expressed in most tissues of higher eukaryotes. These proteins share the unique property of cross-linking actin filaments into tight bundles, and they are primarily involved in regulation of the actin cytoskeleton. L-Plastin is predominantly expressed in hematopoietic cells, but has also been shown to be expressed in most human cancer cells and might be involved in DNA repair, tumor cell migration and invasion (23, 24). In our microarray study, expression of LCP1 in the paclitaxel-resistant MDA-PR cell line was significantly up-regulated by a combination of bexarotene and paclitaxel treatment. This result implies that LCP1 might be involved in the antitumor action exerted by bexarotene. Recent studies have found both actin and tubulin to be involved in tumor cell-resistance to chemotherapy (25-27). Thus, the LCP1 polymorphism identified in this study may causally or functionally influence individual responses to bexarotene as an antitumor agent.

Using DNA extracted from a suboptimal source such as plasma, the genotype call rates in our study are lower than the typical call rates for other genotyping studies where DNA was extracted from optimal DNA sources such as whole blood. Detailed analysis of the genotyping raw data generated from iPLEX assays showed that many of the no calls were due to very low or no signal from either allele, but reliable genotype calls still could be made when signals are substantially higher than background noise (data not shown). Studies from Lu et al. and Park et al. on whole genome amplification samples also showed that high concordance genotype calls could be obtained from samples with low overall call rates (28, 29). In addition, multiple SNPs were genotyped in the same LD block, since it is unlikely that a false positive result would continually arise in subsequent genotyping and analyses. For instance, the four significant SNPs identified in the LD block close to SLC10A2 are unlikely to have been driven by multiple genotyping errors that happen to go in the direction of an association. In addition, some of the genes related to these associated SNPs are related to the functions of bexarotene.

Plasma samples were not collected from patients in the chemotherapy-only control groups. The correlation between survival and triglyceride level induced by bexarotene was observed in two very large, randomized, independent phase III trials (9, 10) which evaluated different chemo therapy agents with or without bexarotene across nearly 250 clinical sites worldwide. The patient populations were very uniform due to the strict inclusion criteria, and all patients had advanced stage IIIb or stage IV NSCLC qualifying for first-line treatment. Moreover, similar correlations between high triglyceride levels and bexarotene efficacy were also revealed by retrospective analysis in other bexarotene phase II lung cancer and renal cell carcinoma trials, as well as trials in cutaneous T cell lymphoma (11).

Overall, the associated SNPs identified from this study provide a new insight for rexinoid-induced hypertriglyceridemia and its antitumor action. These results might eventually lead to development of patient selection criteria to maximize the efficacy of RXR modulators to treat important diseases such as metabolic disorders and cancer. These polymorphisms are also promising candidates for use as genomic markers to predict bexarotene response, and have significant clinical utility.

The above example is included for illustrative purposes only and is not intended to limit the scope of the invention. Many variations to those described above are possible. Since modifications and variations to the examples described above will be apparent to those of skill in this art, it is intended that this invention be limited only by the scope of the appended claims.

REFERENCES

1 Boehm M F, Zhang L, Badea B-A, White S K, Mais D E, Berger E M, Suto C M, Goldman M E and Heyman R A: Synthesis and structure-activity relationships of novel retinoid X receptor-selective retinoids. J of Med Chem 37: 2930-2941, 1994.
2 Duvic M, Hymes K, Heald P, Breneman D, Martin A G, Myskowski P, Crowley C and Yocum R C: Bexarotene is effective and safe for treatment of refractory advanced-stage cutaneous T-cell lymphoma: multinational phase I I-III trial results. J Clin Oncol 19: 2456-2471, 2001.
3 Khuri F R, Rigas J R, Figlin R A, Gralla R J, Shin D M, Munden R, Fox N, Huyghe M R, Kean Y, Reich S D and Hong W K: Multi-institutional phase I/II trial of oral bexarotene in combination with cisplatin and vinorelbine in previously untreated patients with advanced non-small cell lung cancer. J Clin Oncol 19: 2626-2637, 2001.
4 Edelman M J, Smith R, Hausner P, Doyle L A, Kalra K, Kendall J, Bedor M and Bisaccia S: Phase II trial of the novel retinoid, bexarotene, and gemcitabine plus carboplatin in advanced non small cell lung cancer. J Clin Oncol 23: 5774-5778, 2005.
5 Yen W-C and Lamph W W: The selective retinoid X receptor agonist bexarotene (LGD1069, Targretin) prevents and overcomes multidrug resistance in advanced breast carcinoma. Mol Cancer Thera 4: 824-834, 2005.
6 Wu K, Kim H T, Rodriquez J L, Hilsenbeck S G, Mohsin S K, Xu X C, Lamph W W, Kuhn J G, Green J E and Brown P H: Suppression of mammary tumorigenesis in transgenic mice by the RXR-selective retinoid, LGD1069. Cancer Epidemiol Biomarkers Prev 11: 467-474, 2002.
7 Rizvi N A, Marshall J L, Dahut W, Ness E, Truglia J A, Loewen G, Gill G M, Ulm E H, Geiser R, Jaunakais D and Hawkins M J: A Phase I study of LGD1069 in adults with advanced cancer. Clin Cancer Res 5: 1658-1664, 1999.
8 Miller V A, Benedetti F M, Rigas J R, Verret A L, Pfister D G, Straus D, Kris M G, Crisp M, Heyman R, Loewen G R, Truglia J A and Warrell R P, Jr.: Initial clinical trial of a selective retinoid X receptor ligand, LGD1069. J Clin Oncol 15: 790-795, 1997.
8 Ramlau R, Zatloukal P, Jassem J, Schwarzenberger P, Orlov S V, Gottfried M, Pereira J R, Temperley G, Negro-Vilar R, Rahal S, Zhang J K, Negro-Vilar A and Dziewanowska Z E: Randomized phase III trial comparing bexarotene (L1069-49)/cisplatin/vinorelbine with cisplatin/vinorelbine in chemotherapy-naive patients with advanced or metastatic non-small-cell lung cancer: SPIRIT I. J Clin Oncol 26: 1886-1892, 2008.
10 Blumenschein G R, Jr., Khuri F R, von Pawel J, Gatzemeier U, Miller W H, Jr., Jotte R M, Le Treut J, Sun S L, Zhang J K, Dziewanowska Z E and Negro-Vilar A: Phase III trial comparing carboplatin, paclitaxel, and bexarotene with carboplatin and paclitaxel in chemotherapy-naive patients with advanced or metastatic non-small-cell lung cancer: SPIRIT II. J Clin Oncol 26: 1879-1885, 2008.
11 Govindan R, Crowley J, Schwartzberg L, Kennedy P, Williams C, Ekstrand B, Sandler A, Jaunakais D, Bolejack V and Ghalie R: Phase II Trial of Bexarotene Capsules in Patients With Advanced Non-Small-Cell Lung Cancer After Failure of Two or More Previous Therapies. J Clin Oncol 24: 4848-4854, 2006.
12 Purcell S, Neale B, Todd-Brown K, Thomas L, Ferreira M A, Bender D, Maller J, Sklar P, de Bakker P I, Daly M J and Sham P C: PLINK: a tool set for whole-genome association and population-based linkage analyses. Am J Hum Genet 81: 559-575, 2007.
13 Altucci L, Leibowitz M D, Ogilvie K M, de Lera A R and Gronemeyer H: RAR and RXR modulation in cancer and metabolic disease. Nat Rev Drug Discov 6: 793-810, 2007.
14 Pinaire J A and Reifel-Miller A: Therapeutic potential of retinoid x receptor modulators for the treatment of the metabolic syndrome. PPAR Res 2007: 94156, 2007.
15 Chiang J Y: Bile acid regulation of gene expression: roles of nuclear hormone receptors. Endocr Rev 23: 443-463, 2002.
16 Kast H R, Nguyen C M, Sinal C J, Jones S A, Laffitte B A, Reue K, Gonzalez F J, Willson T M and Edwards P A: Farnesoid X-activated receptor induces apolipoprotein C-II transcription: a molecular mechanism linking plasma triglyceride levels to bile acids. Mol Endocrinol 15: 1720-1728, 2001.
17 Watanabe M, Houten S M, Wang L, Moschetta A, Mangelsdorf D J, Heyman R A, Moore D D and Auwerx J: Bile acids lower triglyceride levels via a pathway involving FXR, SHP, and SREBP-lc. J Clin Invest 113: 1408-1418, 2004.
18 Carulli N, Ponz de Leon M, Podda M, Zuin M, Strata A, Frigerio G and Digrisolo A: Chenodeoxycholic acid and ursodeoxycholic acid effects in endogenous hypertriglyceridemias. A controlled double-blind trial. J Clin Pharmacol 21: 436-442, 1981.
19 Duane W C, Hartich L A, Bartman A E and Ho S B: Diminished gene expression of ileal apical sodium bile acid transporter explains impaired absorption of bile acid in patients with hypertriglyceridemia. J Lipid Res 41: 1384-1389, 2000.
20 Love M W, Craddock A L, Angelin B, Brunzell J D, Duane W C and Dawson P A: Analysis of the ileal bile acid transporter gene, SLC10A2, in subjects with familial hypertriglyceridemia. Arterioscler Thromb Vasc Biol 21: 2039-2045, 2001.
21 Jung D, Fried M and Kullak-Ublick G A: Human apical sodium-dependent bile salt transporter gene (SLC10A2)

is regulated by the peroxisome proliferator-activated receptor alpha. J Biol Chem 277: 30559-30566, 2002.
22. Neimark E, Chen F, Li X and Shneider B L: Bile acid-induced negative feedback regulation of the human ileal bile acid transporter. Hepatology 40: 149-156, 2004.
13. Delanote V, Vandekerckhove J and Gettemans J: Plastins: versatile modulators of actin organization in (patho) physiological cellular processes. Acta Pharmacol Sin 26: 769-779, 2005.
24. Samstag Y and Klemke M: Ectopic expression of L-plastin in human tumor cells: diagnostic and therapeutic implications. Adv Enzyme Regul 47: 118-126, 2007.
25. Prislei S, Mozzetti S, Filippetti F, De Donato M, Raspaglio G, Cicchillitti L, Scambia G and Ferlini C: From plasma membrane to cytoskeleton: a novel function for semaphorin 6A. Mol Cancer Ther 7: 233-241, 2008.
26. Gan P P, Pasquier E and Kavallaris M: Class III beta-tubulin mediates sensitivity to chemotherapeutic drugs in non small cell lung cancer. Cancer Res 67: 9356-9363, 2007.
27. Verrills N M, Po'uha S T, Liu M L, Liaw T Y, Larsen M R, Ivery M T, Marshall G M, Gunning P W and Kavallaris M: Alterations in gamma-actin and tubulin-targeted drug resistance in childhood leukemia. J Natl Cancer Inst 98: 1363-1374, 2006.
28. Lu Y, Gioia-Patricola L, Gomez J V, Plummer M, Franceschi S, Kato I and Canzian F: Use of whole genome amplification to rescue DNA from plasma samples. Biotechniques 39: 511-515, 2005.
29. Park J W, Beaty T H, Boyce P, Scott A F and McIntosh I: Comparing whole-genome amplification methods and sources of biological samples for single-nucleotide polymorphism genotyping. Clin Chem 51: 1520-1523, 2005.
30. Cramer P E, Cirrito J R, Wesson D W, Lee C Y, Karlo J C, Zinn A E, Casali B T, Restivo J L, Goebel W D, James M J, Brunden K R, Wilson D A and Landreth G E: ApoE-directed therapeutics rapidly clear β-amyloid and reverse deficits in A D mouse models. Science 335: 1503-1506, 2012.
31. Luo W, Schork N J, Marschke K B, Ng S C, Hermann T W, Zhang J, Sanders J M, Tooker P, Malo N, Zapala M A, Dziewanowska Z E, Negro-Vilar A and Meglasson M D: Identification of polymorphisms associated with hypertriglyceridemia and prolonged survival induced by bexarotene in treating non-small cell lung cancer. Anticancer Res 31: 2303-2311, 2011.

TABLE 1

Baseline characteristics by triglyceride subgroup.

| Parameter | In-treatment triglyceride subgroups | | |
|---|---|---|---|
| | Low (n = 124) | Middle (n = 129) | High (n = 150) |
| Male (%) | 75.8 | 70.5 | 64.7 |
| Age (% in category) | | | |
| ≤60 years | 42.7 | 34.9 | 46.0 |
| >60 years | 57.3 | 65.1 | 54.0 |
| Race (%) | | | |
| Non-White | 8.9 | 8.5 | 5.3 |
| White | 91.1 | 91.5 | 94.7 |
| Region (%) | | | |
| Australia | 0.8 | 3.9 | 2.0 |
| Eastern Europe | 30.6 | 32.6 | 29.3 |
| North America | 33.9 | 32.6 | 40.0 |
| South America | 8.1 | 5.4 | 4.7 |
| Western Europe/Israel | 26.6 | 25.6 | 24.0 |
| Mean baseline triglyceride (in percentile*) | 38.3 | 47.2 | 61.4 |

*Percentiles of baseline triglyceride were calculated among all patients regardless of subgroup.

TABLE 2

Association of SNPs with hypertriglyceridemia in case-control analysis.

| SNP | Gene name | Verification group (n = 141) | | | Replication group (n = 118) | | | Combined group (n = 259) | | |
|---|---|---|---|---|---|---|---|---|---|---|
| | | Case MAF | Control MAF | P-value | Case MAF | Control MAF | P-value | Case MAF | Control MAF | P-value |
| rs7434820 | FLJ46481 | 0.432 | 0.219 | 2.51E−04 | 0.393 | 0.284 | 0.1006 | 0.413 | 0.245 | 1.22E−04 |
| rs4572960* | ITGA1/PELO | 0.348 | 0.645 | 1.53E−06 | 0.382 | 0.537 | 0.0263 | 0.369 | 0.609 | 1.59E−07 |
| rs10058324* | ITGA1/PELO | 0.297 | 0.574 | 1.60E−04 | 0.373 | 0.535 | 0.0197 | 0.335 | 0.552 | 1.59E−05 |
| rs1051853* | SPOCK1 | 0.045 | 0.189 | 1.44E−03 | 0.059 | 0.143 | 0.0450 | 0.052 | 0.165 | 2.53E−04 |
| rs6997581* | CSMD1/MCPH1 | 0.250 | 0.600 | 5.71E−09 | 0.382 | 0.556 | 0.0104 | 0.326 | 0.609 | 3.16E−10 |
| rs2631686* | PCGF5 | 0.272 | 0.500 | 9.24E−05 | 0.400 | 0.543 | 0.0319 | 0.337 | 0.517 | 3.80E−05 |
| rs1795505* | LIN7A | 0.117 | 0.229 | 1.66E−02 | 0.123 | 0.238 | 0.0259 | 0.120 | 0.232 | 1.07E−03 |
| rs1184776* | LIN7A | 0.078 | 0.214 | 1.78E−03 | 0.101 | 0.214 | 0.0203 | 0.090 | 0.214 | 1.12E−04 |
| rs7334509* | CPB2 | 0.490 | 0.346 | 3.50E−02 | 0.592 | 0.372 | 0.0037 | 0.540 | 0.357 | 3.35E−04 |
| rs6491738 | SLC10A2 | 0.234 | 0.455 | 2.11E−04 | 0.291 | 0.386 | 0.1392 | 0.264 | 0.427 | 1.64E−04 |
| rs7333033* | SLC10A2 | 0.261 | 0.458 | 5.61E−04 | 0.268 | 0.404 | 0.0279 | 0.264 | 0.437 | 3.72E−05 |
| rs7338381 | SLC10A2 | 0.254 | 0.444 | 7.91E−04 | 0.268 | 0.383 | 0.0615 | 0.261 | 0.420 | 1.26E−04 |
| rs3916931 | SLC10A2 | 0.225 | 0.431 | 2.36E−04 | 0.261 | 0.362 | 0.0972 | 0.243 | 0.403 | 9.09E−05 |
| rs1506011* | Unknown | 0.589 | 0.246 | 2.33E−08 | 0.393 | 0.238 | 0.0213 | 0.492 | 0.243 | 3.88E−08 |

Associations were calculated with two-allele model in the case-control test. The p-values which were lower than 0.05 are highlighted in bold, and the associated SNPs whose p-values are lower than 0.05 in all three tests are with asterisks. Minor allele frequency (MAF) for case and control are listed under the corresponding columns.

TABLE 3

Association of SNPs with hypertriglyceridemia using quantitative trait analysis.

| SNP | Chr. | Position | Gene name | Verification group (n = 141) Mean TRIG AA/AB/BB | P-value | Replication group (n = 244) Mean TRIG AA/AB/BB | P-value | Combined group (n = 385) Mean TRIG AA/AB/BB | P-value |
|---|---|---|---|---|---|---|---|---|---|
| rs7434820* | 4 | 6081537 | FLJ46481 | 41/56/66 | 1.21E−03 | 46/50/54 | 0.0489 | 44/53/58 | 2.34E−04 |
| rs4572960* | 5 | 51608341 | ITGA1/PELO | 64/49/30 | 1.54E−05 | 56/48/47 | 0.0245 | 59/48/40 | 1.52E−06 |
| rs10058324* | 5 | 51679280 | ITGA1/PELO | 44/58/71 | 2.65E−03 | 46/47/55 | 0.0243 | 45/50/61 | 1.28E−04 |
| rs1051853* | 5 | 136341700 | SPOCK1 | NA§/29/62 | 3.66E−03 | 26/45/50 | 0.0182 | 36/39/54 | 3.42E−04 |
| rs6997581* | 8 | 5321568 | CSMD1/MCPH1 | 63/65/28 | 1.18E−07 | 52/52/43 | 0.0171 | 55/57/36 | 4.71E−08 |
| rs2631686 | 10 | 93043517 | PCGF5 | 28/48/58 | 3.00E−04 | 43/53/50 | 0.0722 | 38/51/54 | 1.27E−04 |
| rs1795505* | 12 | 79771464 | LIN7A | 53/30/40 | 3.38E−02 | 52/48/41 | 0.0502 | 52/41/41 | 3.76E−03 |
| rs1184776* | 12 | 79776533 | LIN7A | 53/33/29 | 5.46E−03 | 52/43/43 | 0.0247 | 52/39/39 | 3.71E−04 |
| rs7334509 | 13 | 45590412 | CPB2 | 43/50/63 | 6.17E−02 | 40/52/52 | 0.0041 | 41/51/55 | 1.17E−03 |
| rs6491738* | 13 | 102769437 | SLC10A2 | 59/41/34 | 9.67E−04 | 52/50/43 | 0.0395 | 55/46/40 | 1.49E−04 |
| rs7333033* | 13 | 102776263 | SLC10A2 | 59/41/37 | 1.54E−03 | 52/50/40 | 0.0077 | 55/47/39 | 3.18E−05 |
| rs7338381* | 13 | 102776418 | SLC10A2 | 58/41/38 | 3.79E−03 | 52/51/40 | 0.0141 | 54/47/39 | 1.38E−04 |
| rs3916931* | 13 | 102784358 | SLC10A2 | 59/42/33 | 7.04E−04 | 53/48/43 | 0.0221 | 55/46/40 | 6.15E−05 |
| rs1506011 | 21 | 23490212 | Unknown | 32/50/75 | 1.47E−07 | 48/48/57 | 0.1491 | 43/49/66 | 1.28E−06 |

§ NA: No mean available because there is only one sample in this genotype.
The p-values which are lower than 0.05 are highlighted in bold, and the associated SNPs that met this threshold in all three tests are indicated with an asterisk.
The two alleles are represented by A and B, thus homozygous are AA and BB, and heterozygous are represented by AB. Average of triglyceride levels in patients carrying the indicated genotype are listed under "Mean TRIG" column.

The invention claimed is:

1. A method, comprising:
   a) obtaining a biological sample from a subject that is undergoing a cancer treatment with a retinoid X receptor (RXR) modulator, or is considered for the cancer treatment;
   b) isolating genomic DNA from said biological sample;
   c) assaying a biomarker or a panel of biomarkers in the isolated genomic DNA,
   wherein the biomarker or panel consists of one or more single nucleotide polymorphisms (SNPs) selected from the group consisting of rs7434820, rs4572960, rs10058324, rs1051853, rs6997581, rs2631686, rs1795505, rs1184776, rs7334509, rs6491738, rs7333033, rs7338381, rs3916931, and rs1506011, or a complementary sequence thereof, and
   wherein the method does not comprise assaying any other SNP.

2. The method of claim 1, wherein the biomarker is or the panel are assayed by sequencing, capillary electrophoresis, mass spectrometry, single-strand conformation polymorphism (SSCP), electrochemical analysis, denaturing HPLC and gel electrophoresis, restriction fragment length polymorphism, hybridization analysis, single-base extension, and/or microarray.

3. The method of claim 1, wherein the cancer treatment further comprises a therapeutic regimen using a modulator of a retinoid acid receptor (RAR), a peroxisome proliferator-activated receptor (PPAR), a Liver X receptor (LXR), or a farnesoid X receptor (FXR).

4. The method of claim 1, wherein the RXR modulator is bexarotene.

5. The method of claim 1, wherein the cancer is selected from the group consisting of non-small cell lung cancer (NSCLC), small cell lung cancer, prostate cancer, breast cancer, renal cell carcinoma, and cutaneous T-cell lymphoma.

6. The method of claim 1, wherein the panel of biomarkers comprises two or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, and rs1506011, or complementary sequences thereof.

7. The method of claim 1, wherein the panel of biomarkers comprises three or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, and rs1506011, or complementary sequences thereof.

8. The method of claim 1, wherein the panel of biomarkers comprises four or more SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, and rs1506011, or complementary sequences thereof.

9. The method of claim 1, wherein the panel of biomarkers comprises all of the SNPs selected from the group consisting of rs7434820, rs4572960, rs10058324, rs1051853, rs6997581, rs2631686, rs1795505, rs1184776, rs7334509, rs6491738, rs7333033, rs7338381, rs3916931, and rs1506011, or complementary sequences thereof.

10. The method of claim 1, wherein the SNPs comprise the nucleotide sequences set forth in SEQ ID NOs: 1-14, respectively, or complementary sequences thereof.

11. The method of claim 1, wherein the biomarker or panel is assayed using a microarray comprising a combination of molecules on a substrate, wherein said molecules are used for assaying the SNPs.

12. The method of claim 11, wherein the molecules are oligonucleotides or polypeptides.

13. The method of claim 12, wherein the oligonucleotides comprise the nucleotide sequences set forth in SEQ ID NOs: 1-14, or complementary sequences thereof.

14. The method of claim 1, wherein the biomarker or panel is assayed using a reagent or a kit for assaying the SNPs.

15. The method of claim 14, wherein the reagent or kit comprises one or more molecules for assaying the SNPs.

16. The method of claim 15, wherein the molecule is an oligonucleotide or a polypeptide.

17. The method of claim 16, wherein the oligonucleotide comprises a nucleotide sequence set forth in SEQ ID NOs: 1-14, or a complementary sequence thereof.

18. The method of claim 1, wherein each of the SNPs is associated with the triglyceride level in the subject under cancer treatment with the RXR modulator.

* * * * *

SEQUENCE LISTING

<160> NUMBER OF SEQ ID NOS: 14

<210> SEQ ID NO 1
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs7434820
<220> FEATURE:
<221> NAME/KEY: misc_feature
<222> LOCATION: 27
<223> OTHER INFORMATION: n = c/t

<400> SEQUENCE: 1
cgagtgatag gatgaggcta atgatanaga gggcgaaaca tctcctcatt ca            52

<210> SEQ ID NO 2
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs4572960
<220> FEATURE:
<221> NAME/KEY: misc_feature
<222> LOCATION: 27
<223> OTHER INFORMATION: n = a/c/t

<400> SEQUENCE: 2
ctctccaaaa taactcttca tgcacanttt agcttacctc tgaaaaacta ca            52

<210> SEQ ID NO 3
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP)  rs10058324
<220> FEATURE:
<221> NAME/KEY: misc_feature
<222> LOCATION: 27
<223> OTHER INFORMATION: n = a/g

<400> SEQUENCE: 3
gcagacaaaa taacatcttt aacacancat ctccgataaa aagattcaaa ag          52

<210> SEQ ID NO 4
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs10058324
<220> FEATURE:
<221> NAME/KEY: misc_feature
<222> LOCATION: 27
<223> OTHER INFORMATION: n = a/g

<400> SEQUENCE: 4
gcagacaaaa taacatcttt aacacancat ctccgataaa aagattcaaa ag          52

<210> SEQ ID NO 5
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs6997581
<220> FEATURE:
<221> NAME/KEY: misc_feature
<222> LOCATION: 27
<223> OTHER INFORMATION: n = c/t

<400> SEQUENCE: 5
aaatgcacac ctaacgcaca ttcctgnggt ccaagacagc atgattccag ag          52

<210> SEQ ID NO 6
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs2631686
<220> FEATURE:
<221> NAME/KEY: misc_feature
<222> LOCATION: 27
<223> OTHER INFORMATION: n = c/t

<400> SEQUENCE: 6
caagcagccc ttcctgtctt agcctanaca tcattaccta ataagcaaac ct          52

<210> SEQ ID NO 7
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs1795505
<220> FEATURE:
<221> NAME/KEY: misc_feature
<222> LOCATION: 27
<223> OTHER INFORMATION: n = c/g

<400> SEQUENCE: 7
catccataaa attacgttta cagtagntga aggtaccaaa tggatcagtc tc          52

<210> SEQ ID NO 8
<211> LENGTH: 52
<212> TYPE: DNA

<213> ORGANISM: Artificial Sequence
<220> FEATURE:
<223> OTHER INFORMATION: synthetically constructed single nucleotide
      polymorphism (SNP) rs1184776
<220> FEATURE:
<221> NAME/KEY: misc_feature
<222> LOCATION: 27
<223> OTHER INFORMATION: n = c/t

<400> SEQUENCE: 8
gagaggttta ttcatggatg gacttcnttg tagatgttag gtcaaaaaaa aa         52

<210> SEQ ID NO 9
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs7334509
<220> FEATURE:
<221> NAME/KEY: misc_feature
<222> LOCATION: 27
<223> OTHER INFORMATION: n= a/g

<400> SEQUENCE: 9
tgctcataat gcttaccatg ccatggntaa tagagttctt tgccatagac ct         52

<210> SEQ ID NO 10
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs6491738
<220> FEATURE:
<221> NAME/KEY: misc_feature
<222> LOCATION: 27
<223> OTHER INFORMATION: n = c/t

<400> SEQUENCE: 10
atccatctcc ttccatcctc agacatnggc actcgtggtt cttgggcctt ca         52

<210> SEQ ID NO 11
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs7333033
<220> FEATURE:
<221> NAME/KEY: misc_feature
<222> LOCATION: 27
<223> OTHER INFORMATION: n = a/c

<400> SEQUENCE: 11
caagccttaa tccatgagac agatgtnttg gttttctcac ttctttgggt ca         52

<210> SEQ ID NO 12
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs7338381
<220> FEATURE:
<221> NAME/KEY: misc_feature
<222> LOCATION: 27
<223> OTHER INFORMATION: n = a/g

<400> SEQUENCE: 12

```
aatgtttgct ctagattctt aaggccnctg ttcttttcag catgatttta ct                52

<210> SEQ ID NO 13
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs3916931
<220> FEATURE:
<221> NAME/KEY: misc_feature
<222> LOCATION: 27
<223> OTHER INFORMATION: n = a/t

<400> SEQUENCE: 13
gaggagaatg aggatctgac acaaagnaag attattattt cctgcaacaa ga               52

<210> SEQ ID NO 14
<211> LENGTH: 52
<212> TYPE: DNA
<213> ORGANISM: Artificial Sequence
<220> FEATURE:
<223> OTHER INFORMATION: synthetically constructed single nucleotide
      polymorphism (SNP) rs1506011
<220> FEATURE:
<221> NAME/KEY: misc_feature
<222> LOCATION: 27
<223> OTHER INFORMATION: n = a/g

<400> SEQUENCE: 14
atgtaacata gtgatgattg aaacccnaaa tataaatgaa tgccacataa tg               52
```